(12) United States Patent
Mulligan et al.

(10) Patent No.: US 7,164,992 B1
(45) Date of Patent: Jan. 16, 2007

(54) METHOD AND SYSTEM FOR POLYNUCLEOTIDE SYNTHESIS

(75) Inventors: John T. Mulligan, Seattle, WA (US); John C. Tabone, Bothell, WA (US); R. Gregg Brickner, Seattle, WA (US)

(73) Assignee: Blue Heron Biotechnology, Inc., Bothell, WA (US)

( * ) Notice: Subject to any disclaimer, the term of this patent is extended or adjusted under 35 U.S.C. 154(b) by 347 days.

(21) Appl. No.: 10/104,986

(22) Filed: Mar. 22, 2002

Related U.S. Application Data

(60) Provisional application No. 60/278,086, filed on Mar. 22, 2001, provisional application No. 60/278,067, filed on Mar. 22, 2001.

(51) Int. Cl.
G06F 19/00 (2006.01)
G11C 17/00 (2006.01)
G05B 15/00 (2006.01)

(52) U.S. Cl. .............................. 702/20; 365/94; 700/1

(58) Field of Classification Search ............ 702/19–20; 703/11; 707/102
See application file for complete search history.

(56) References Cited

U.S. PATENT DOCUMENTS

| | | | | |
|---|---|---|---|---|
| 4,652,639 | A | 3/1987 | Stabinsky | .................. 536/27 |
| 5,942,609 | A | 8/1999 | Hunkapiller et al. | ....... 536/25.3 |
| 6,521,427 | B1 * | 2/2003 | Evans | ........................ 435/91.1 |
| 6,670,127 | B1 * | 12/2003 | Evans | ........................... 435/6 |

FOREIGN PATENT DOCUMENTS

| | | |
|---|---|---|
| WO | WO 98/15567 | 4/1998 |
| WO | WO 99/14318 | 3/1999 |

OTHER PUBLICATIONS

Withers-Martinez et al. PCR-based gene synthesis as an efficient approach for expression of the A+T-rich malaria genome. Protein Engineering, vol. 12, pp. 1113-1120 (1999).*
Jerala et al., "Regen: program for designing gene assembly," *Nucleic Acids Research* 16(5):1759-1766, 1988.
Libertini et al., "Computer-aided gene design," *Protein Engineering* 5(8):821-825, 1992.
Makarova et al., "DIROM'-an interactive system for planning experiments on directed mutagenesis and design of artificial genes," *Mol Biol (Mosk)* 26(1):93-103, 1992.

* cited by examiner

*Primary Examiner*—John S. Brusca
(74) *Attorney, Agent, or Firm*—Seed IP Law Group PLLC

(57) ABSTRACT

Methods and systems for automated polynucleotide synthesis design are provided. Example embodiments provide an Automated Polynucleotide Synthesis Design System ("APSDS"), which automatically generates a synthesis design for a designated target sequence specification. In one embodiment, the APSDS comprises a synthesis design engine, user interface support, a synthesis rules data repository, and a synthesis data repository. The APSDS automatically generates a synthesis design by receiving a target sequence(s) specification, generating a potential synthesis design, evaluating the potential design against synthesis rules, and when the evaluation indicates that the potential design is not successful according to the synthesis rules, adjusting the design to generate a new potential synthesis design and repeating the process of evaluating and adjusting until a potential synthesis design is found that satisfies the synthesis rules or until no solution is found.

41 Claims, 26 Drawing Sheets

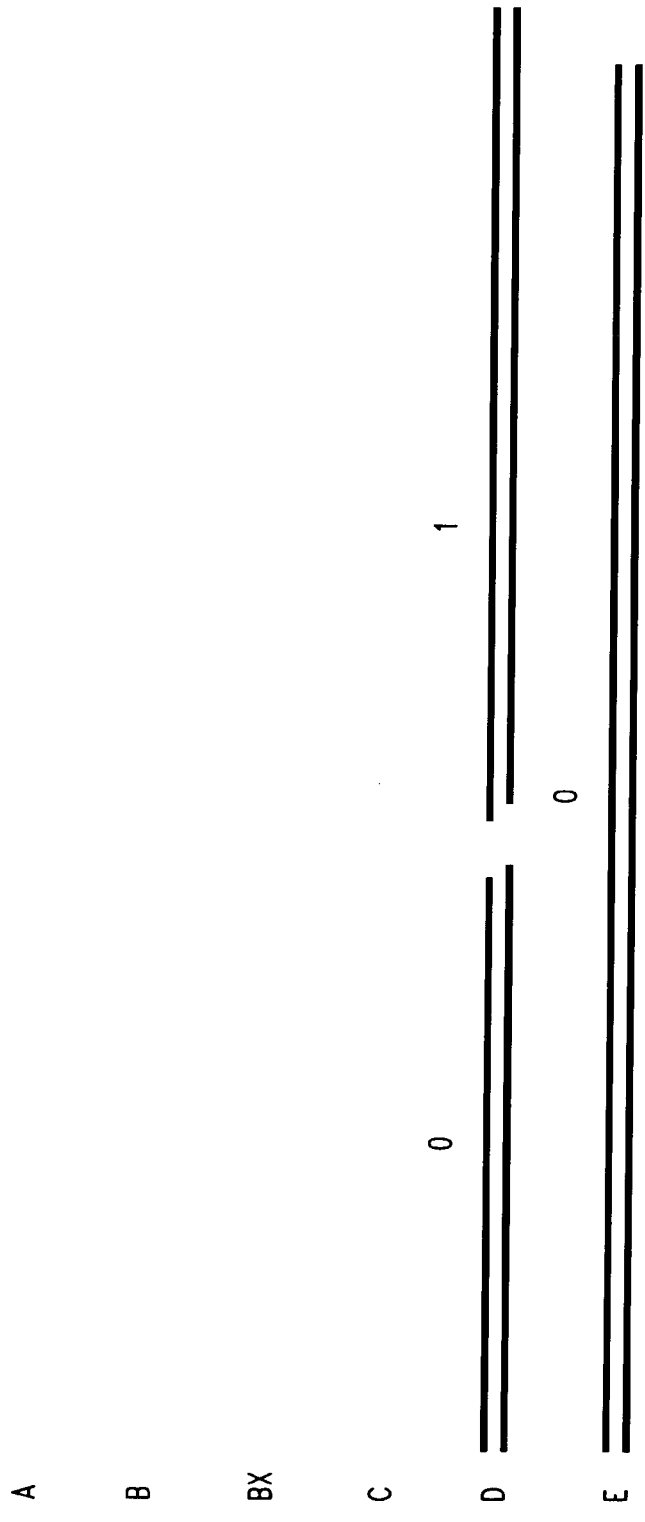

SEQUENCE LISTING

```
<160> NUMBER OF SEQ ID NOS: 12

<210> SEQ ID NO 1
<211> LENGTH: 25
<212> TYPE: DNA
<213> ORGANISM: Artificial Sequence
<220> FEATURE:
<223> OTHER INFORMATION: Random generated example

<400> SEQUENCE: 1
```
cctgagagga cagtcaatca cagga                                    25

<210> SEQ ID NO 2
<211> LENGTH: 25
<212> TYPE: DNA
<213> ORGANISM: Artificial Sequence
<220> FEATURE:
<223> OTHER INFORMATION: Random generated example

<400> SEQUENCE: 2
ggactgtcct gtcagttagt gtcct                                    25

<210> SEQ ID NO 3
<211> LENGTH: 10
<212> TYPE: DNA
<213> ORGANISM: Artificial Sequence
<220> FEATURE:
<223> OTHER INFORMATION: Random generated example

<400> SEQUENCE: 3
ggacagtcaa                                                     10

<210> SEQ ID NO 4
<211> LENGTH: 10
<212> TYPE: DNA
<213> ORGANISM: Artificial Sequence
<220> FEATURE:
<223> OTHER INFORMATION: Random generated example

<400> SEQUENCE: 4
ttgactgtcc                                                     10

<210> SEQ ID NO 5
<211> LENGTH: 25
<212> TYPE: DNA
<213> ORGANISM: Artificial Sequence
<220> FEATURE:
<223> OTHER INFORMATION: Random generated example

<400> SEQUENCE: 5
cctgagagga cagtcaatca cagga                                    25

<210> SEQ ID NO 6
<211> LENGTH: 21
<212> TYPE: DNA
<213> ORGANISM: Artificial Sequence
<220> FEATURE:
<223> OTHER INFORMATION: Random generated example

<400> SEQUENCE: 6
tgtcctgtca gttagtgtcc t                                        21

<210> SEQ ID NO 7
<211> LENGTH: 21
<212> TYPE: DNA
<213> ORGANISM: Artificial Sequence
<220> FEATURE:
<223> OTHER INFORMATION: Random generated example

<400> SEQUENCE: 7
cctgagagga cagtcaatca c                                        21

<210> SEQ ID NO 8
<211> LENGTH: 11
<212> TYPE: DNA

```
<213> ORGANISM: Artificial Sequence
<220> FEATURE:
<223> OTHER INFORMATION: Random generated example

<400> SEQUENCE: 8
cctgagagga c                                                          11

<210> SEQ ID NO 9
<211> LENGTH: 11
<212> TYPE: DNA
<213> ORGANISM: Artificial Sequence
<220> FEATURE:
<223> OTHER INFORMATION: Random generated example

<400> SEQUENCE: 9
tctcctgtca g                                                          11

<210> SEQ ID NO 10
<211> LENGTH: 10
<212> TYPE: DNA
<213> ORGANISM: Artificial Sequence
<220> FEATURE:
<223> OTHER INFORMATION: Random generated example

<400> SEQUENCE: 10
agtcaatcac                                                            10

<210> SEQ ID NO 11
<211> LENGTH: 10
<212> TYPE: DNA
<213> ORGANISM: Artificial Sequence
<220> FEATURE:
<223> OTHER INFORMATION: Random generated example

<400> SEQUENCE: 11
ttagtgggac                                                            10

<210> SEQ ID NO 12
<211> LENGTH: 21
<212> TYPE: DNA
<213> ORGANISM: Artificial Sequence
<220> FEATURE:
<223> OTHER INFORMATION: Random generated example

<400> SEQUENCE: 12
tctcctgtca gttagtggga c                                               21
```

METHOD AND SYSTEM FOR POLYNUCLEOTIDE SYNTHESIS

BACKGROUND OF THE INVENTION

1. Field of the Invention

The present invention relates to methods and systems for synthesizing polynucleotides and, in particular, to methods and systems for automatically determining synthesis designs that minimize incorrect results.

2. Background Information

While it is currently possible to achieve in vitro synthesis of genes and other long polynucleotides, the time and effort required for preparing these polynucleotides causes bottlenecks in current genetic research. With the recent genome mapping achieved by the Human Genome Project, the desire for such polynucleotides has increased dramatically. There is thus an increased desire to synthesize sequences of genes rather than generating sequences using traditional molecular biology methods for modifying or cloning genetic sequences. The efficient and cost-effective synthesis of genes is of paramount interest in projects that can take otherwise take months to set up. Moreover, certain experiments become more feasible, such as those in which a researcher can cost effectively and quickly test multiple variants of a gene to find one that works for the desired purpose. In addition, some gene sequences are far too long to synthesize using traditional techniques.

The following definitions and conventions for referring to gene synthesis terminology are used herein to facilitate description. Additional background information is available in *Molecular Biology of the Cell*, Third Edition. Alberts, et.al., Garland Publishing, Inc., New York and London, 1994, which is herein incorporated by reference in its entirety. A polynucleotide is formed from a plurality of nucleotides, each nucleotide formed from a phosphate, a sugar (deoxyribose), and an organic base—where the base is selected from the purine bases adenine ("A") and guanine ("G") and the pyrimidine bases thymidine ("T") and cytosine ("C"). Because the sugar is deoxyribose, the nucleotides may be referred to deoxyribonucleotides, and the polynucleotide may be referred to as a deoxyribonucleic acid molecule, or DNA. A DNA molecule may be single-stranded or may hybridize to (also referred to as "anneal to" or "anneal with") another DNA molecule to form a double-stranded structure, where the double-stranded structure may also be referred to as a DNA molecule.

The term "gene" as used herein refers to a double-stranded DNA molecule, where the two strands may be distinguished from one another by referring to one strand as the upper or top strand and the other strand as the lower or bottom strand. Thus, either of the terms "gene" or "DNA molecule" may be used to denote any long, double-stranded polynucleotide, where a long polynucleotide contains at least 100 nucleotides. In simplified explanation, gene synthesis is the production of double-stranded DNA molecules from, typically, a text specification of a single-stranded target sequence. Each single-stranded DNA molecule (and thus nucleotide sequence) has two ends (termini), and is associated with a direction (or "handedness"). One of the two termini is referred to as the 3' end while the other termini is referred to as the 5' end. A terminal hydroxyl group of a sugar is normally located at the 3' end of the molecule, and a terminal phosphate group is normally located at the 5' end of the molecule. A single strand sequence of DNA is also referred to as a "polynucleotide sequence" or, if the sequence is less than 100 nucleotides, then the polynucleotide sequence may optionally be referred to as an "oligonucleotide" or "oligo." A textual representation of a 25-base pair double-stranded DNA molecule is written in this description as:

5' CCTGAGAGGACAGTCAATCACAGGA 3' (top strand) (SEQ ID NO:1)
3' GGACTGTCCTGTCAGTTAGTGTCCT 5' (bottom strand) (SEQ ID NO:2)

Under appropriate conditions, a base in a single-stranded DNA sequence typically forms hydrogen bonds to a second base in another single-stranded DNA sequence when the pair of bases (one from each strand) are complements of each other. (Specifically, an "A" bonds with a "T" and a "C" bonds with a "G.") Thus a single strand of DNA binds to another strand of DNA to form a double-stranded DNA molecule when each pair of bases of the sequences (one from each strand) is exactly complementary. A double-stranded sequence of DNA is known as a "fragment" or "DNA fragment." Thus, a DNA fragment is a duplex polymer formed from deoxyribonucleic acid molecules. A DNA fragment may be entirely double-stranded, or may contain both single-stranded and double-stranded regions. The DNA fragments may be, for example, portions of a gene or fragments that when joined form a larger portion of the gene or the entire gene.

Hybridization (annealing) refers to this process of joining of oligos or polynucleotides (both as single-stranded DNA sequences) to generate fragments (double-stranded DNA molecules), and is written herein as:

5' GGACAGTCAA 3'+5' TTGACTGTCC 3'→(SEQ ID NO:3) (SEQ ID NO:4)
5' GGACAGTCAA 3' (SEQ ID NO:3)
3' CCTGTCAGTT 5' (SEQ ID NO:4)

Typically, hybridization of single-stranded DNA sequences occurs at low temperature conditions. As the temperature is raised, the double-stranded structure "melts" to form two non-hybridized single-stranded structures.

Once annealed, the resulting double-stranded DNA sequence (or molecule) may have an overhang on one (left or right) or on both sides. For example, a double-stranded DNA sequence with a 5' overhang on the left can be denoted as:

5'CCTGAGAGGACAGTCAATCACAGGA 3' (SEQ ID NO:5)
3' TGTCCTGTCAGTTAGTGTCCT 5' (SEQ ID NO:6)

Or, for example, a double-stranded DNA sequence with a 5' overhang on both the left and right can be denoted as:

5'CCTGAGAGGACAGTCAATCAC 3' (SEQ ID NO:7)
3' TGTCCTGTCAGTTAGTGTCCT 5' (SEQ ID NO:6)

Other double-stranded DNA sequences may be formed with 3' overhangs or combinations of 3' and 5' overhangs, or even with no overhangs in which case the ends are referred to as "blunt" ends. The overhang length refers to the number of bases that form the particular overhang. So, for example, in either DNA sequence represented above, the overhang length of the left end is 4 (bases).

DNA fragments can be further combined through a process referred to as ligation to form longer length fragments, which can ultimately constitute a gene. Ligation is a higher temperature process whereby, with the assistance of an enzyme (referred to as a ligase), DNA fragments in solution are covalently joined together. The presence of overhanging ends facilitates this process, and ends that are reverse complements of each other tend to bond. For example, fragments:

5' CCTGAGAGGAC 3' (SEQ ID NO:8)
3' TCTCCTGTCAG 5' (SEQ ID NO:9)
and
5' AGTCAATCAC 3' (SEQ ID NO:10)
3' TTAGTGGGAC 5' (SEQ ID NO:11)

can be ligated to produce the new fragment:
5'CCTGAGAGGACAGTCAATCAC 3' (SEQ ID NO:7)
3' TCTCCTGTCAGTTAGTGGGAC 5' (SEQ ID NO:12)

According to the standard method of gene synthesis, which may be referred to as the shotgun method of gene synthesis, multiple single-stranded polynucleotide sequences are mixed together in order that they can undergo hybridization to form fragments of (double-stranded) sequences. These fragments have overhangs that are designed to be exactly complementary to overhangs present in other fragments, where the exactly complementary overhangs direct two fragments to hybridize together. The hybridized fragments are then exposed to a ligase to achieve ligation between the adjacent fragments. All of this occurs in a single biochemical reaction. Since many fragments are combined in a single ligation reaction, errors are common and may result in incorrect or undesired synthetic gene sequences.

BRIEF SUMMARY OF THE INVENTION

In one aspect, embodiments of the present invention provide computer- and network-based methods and systems for automatically generating a polynucleotide synthesis design for the synthesis of one or more target double-stranded polynucleotide molecules (deoxyribonucleic acid, or "DNA" molecules). In one embodiment, the techniques of the present invention are used to generate designs for the convergent synthesis of polynucleotide sequences, which are optimized to minimize synthesis errors that may occur through undesired ligations. Convergent synthesis is used to create a gene by ligating double-stranded fragments in a (group-wise) hierarchical order so as to minimize incorrect joining of fragments. A polynucleotide synthesis design specifies what oligos and fragments should be generated, and in what order they may be ligated, in order to achieve a desired target sequence(s). In another embodiment, the techniques of the methods and systems of the present invention are extended and modified to include automatically generating synthesis designs for use with other types of synthesis such as solid phase synthesis, shotgun synthesis, and gapped synthesis.

The automated synthesis design process receives a target (designated) polynucleotide sequence specification, decomposes (deconstructs) the target sequence specification, and, using a set of synthesis heuristics (criteria), generates a synthesis design that indicates the set of oligos (and fragments) that need to be synthesized and the order in which they should be ligated to correctly generate the target sequence(s). In one such embodiment, the synthesis design process automatically designs, whenever possible, a group of fragments that can be later synthesized to create a target sequence such that no two incorrect fragment ends can join in a ligation reaction. In some embodiments, different potential synthesis designs are "scored" to indicate a level of success.

In one embodiment, the design process decomposes the target sequence into a series of double-stranded potential fragments, automatically determines whether the potential fragments meet a synthesis criteria, automatically adjusts the potential fragments until they meet the synthesis criteria or until no more adjustments are possible, and outputs a synthesis design that indicates the adjusted potential fragments as fragments that can be used to synthesize a double-stranded polynucleotide molecule defined by the target sequence.

In one embodiment, the synthesis criteria are rules that assist in determining whether a particular synthesis step will be successful. In one such embodiment, the synthesis rules are ligation rules that check, based upon ends of fragments to be ligated, whether a ligation will occur. In another such embodiment, the synthesis rules are derived empirically. In yet another such embodiment, they are dependent upon the synthesis technique being used. In another such embodiment, they are independent of the synthesis technique. In one embodiment, the synthesis rules check for full matches of fragment overhangs. In another embodiment, the synthesis rules check for partial matches of fragment overhangs. In one such embodiment, the partial match detects whether 3 of 4 base pairs are complementarity. In another such embodiment, the partial match detects whether 6 of 9 base pairs are complementary. In one embodiment, the synthesis rules check for the presence of GC combination base pairs.

In some embodiments, the synthesis criteria determine whether fragment ends will properly ligate by checking for approximate complementarity as well as exact complementarity. In one such embodiment, a base pair is approximate complementarity if it is a "C/T" or "G/T" base pair. In another embodiment, an end is approximately complementary to another end, if the ends behave as though they were exactly complementary. In these embodiments, a full match of base pairs of fragment overhangs occurs when all of the base pairs are either exactly complementary or approximately complementary. Also, a partial match of base pairs of fragment overhangs occurs when a portion of all of the base pairs are either exactly complementary or approximately complementary.

In one embodiment, an Automated Polynucleotide Synthesis Design System ("APSDS") is provided. The APSDS comprises a synthesis design engine, user interface support, a synthesis rules data repository, and a synthesis data repository. The synthesis design engine automatically generates a synthesis design by receiving a target sequence(s) specification, generating a potential synthesis design, evaluating the potential design against synthesis rules, and when the evaluation indicates that the potential design is not successful according to the synthesis rules, adjusting the design to generate a new potential synthesis design and repeating the process of evaluating and adjusting until a potential synthesis design is found that satisfies the synthesis rules or until no solution is found.

In one embodiment, adjusting the design comprises changing fragment specifications, so as to adjust attributes of a plurality of potential joints. Parameters such as a desired default oligo length, joint position, overhang type, and overhang length can be varied and adjusted to change the specification of the fragments (the potential design), hence the joint attributes.

In one embodiment, the synthesis rules are coded into the design engine. In another embodiment, the synthesis rules are retrieved from a data repository. In one such embodiment, the synthesis rules are dynamically configured.

In one such embodiment, the synthesis design engine directly or indirectly controls instruments that carry out the synthesis process. The control may be accomplished by generating instrument-specific commands automatically as part of the design. In other embodiments, the control is accomplished by communicating to another software module, such as a scheduling and synthesis control module.

In one embodiment, the synthesis design comprises a build map, which describes the fragments to be synthesized and the order that the fragments should be ligated to produce the target sequence(s). In another embodiment, the synthesis design is generated according to a particular synthesis technique. In one embodiment, the APSDS automatically generates a synthesis design for use with convergent synthesis techniques, which ligates groups of designed fragments in a hierarchical order. In another embodiment, the generated design is used to control the synthesis process of some or all of the target sequence(s).

In one embodiment, configurable parameters can be input to the synthesis design process, such as a specification of a desired target DNA sequence and/or control parameters that affect the synthesis design process, such as desired oligo length. In one such embodiment, the user interface support provides a secure web-based client interface over, for example, a network such as the Internet.

In another aspect, the present invention provides a method of gene synthesis wherein a plurality of distinct relatively small DNA fragments, e.g., two DNA fragments, are combined together under ligation conditions to provide a (preferably one) relatively large DNA fragment sequence (of course, there will be many DNA fragments of that particular sequence). In one embodiment, this plurality is two, while in another embodiment this plurality is three. Subsequently, a plurality of distinct relatively large DNA fragments, each as prepared above, is combined together under ligation conditions to provide a relatively larger DNA fragment. The process of combining selected smaller DNA fragments together to make a larger DNA fragments, and repeating this with different small DNA fragments to make another larger DNA fragment, and then combining selected larger DNA fragments together to make a set of still larger DNA fragments can be repeated as needed to prepare the desired gene. This process can be referred to as convergent approach to gene synthesis, and is illustrated in FIG. 3 wherein 9 "smaller" DNA fragments are, in separate reaction vessels, combined into 5 "larger" DNA fragments, 2 of these 5 larger DNA fragments are combined into 1 "still larger" DNA fragment, this 1 still larger DNA fragment and the remaining 3 larger DNA fragments are, in two reaction vessels, combined to form 2 largest DNA fragments, and these 2 largest DNA fragments are combined to form the gene. This process is also illustrated in FIGS. 6A–6K.

In a convergent synthesis approach, the final gene is formed by combining at least two DNA fragments, where at least two of these "at least two" DNA fragments where themselves formed by combining at least two DNA fragments. This is to be contrast with a serial approach to gene synthesis, where a first DNA fragment is ligated to a second DNA fragment to provide a first ligation product, the first ligation product is ligated to a third DNA fragment to provide a second ligation product, and the second ligation product is ligated to a fourth DNA fragment to form the final gene.

BRIEF DESCRIPTION OF THE DRAWINGS

FIGS. 6A–6K are example schematic diagrams of the fragments tested and adjusted at each level in an example APSDS used to generate a convergent synthesis design.

DETAILED DESCRIPTION OF THE INVENTION

Embodiments of the present invention provide computer- and network-based methods and systems for automatically generating a polynucleotide synthesis design for the synthesis of one or more target double-stranded polynucleotide sequences (deoxyribonucleic acid, or "DNA" molecules). In one embodiment, the techniques of the present invention are used to generate designs for the convergent synthesis of polynucleotide sequences, which are optimized to minimize synthesis errors that may occur through undesired ligations. Convergent synthesis, as will be described in detail below, is used to create a gene by ligating double-stranded fragments in a (pair-wise) hierarchical order so as to minimize incorrect joining of fragments. As used herein, a polynucleotide synthesis design specifies what oligos and fragments should be generated, and in what order they may be ligated, in order to achieve a desired target sequence(s). Although discussed primarily with respect to convergent synthesis, one skilled in the art will recognize that the techniques of the methods and systems described herein can be extended and modified to include automatically generating synthesis designs for use with other types of synthesis such as solid phase synthesis, shotgun synthesis, and gapped synthesis.

Example embodiments provide automated synthesis design of target sequences through an Automated Polynucleotide Synthesis Design System ("APSDS"). The APSDS takes as input a target (designated) polynucleotide sequence specification, decomposes (deconstructs) the target sequence specification, and, using a set of heuristics and criteria, generates the set of oligos (and fragments) that need to be synthesized and the order in which they should be ligated to correctly generate the target sequence(s). The generated design can then be used to control the synthesis process of some or all of the target sequence(s).

Figure 1:
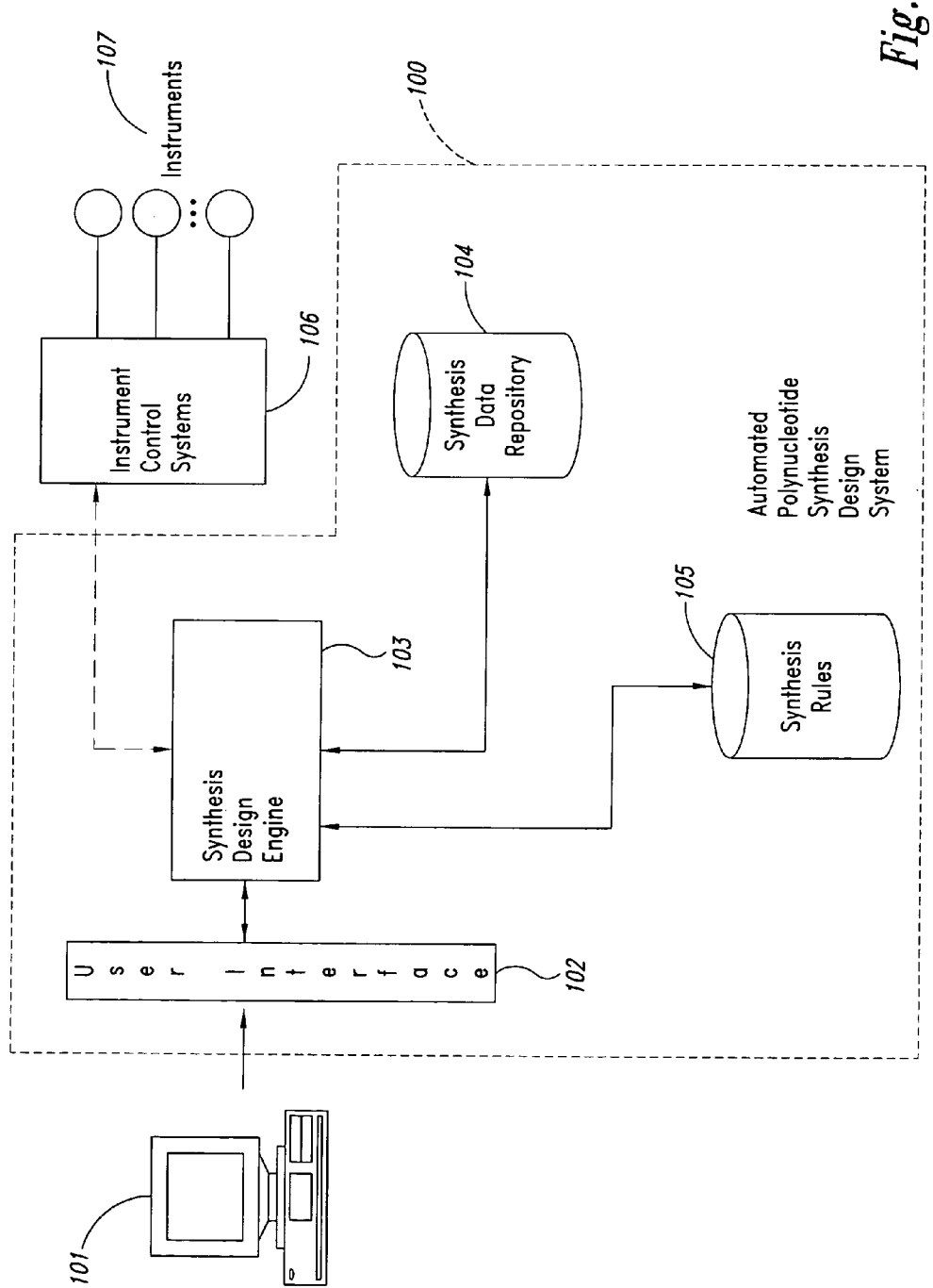
FIG. 1 is an example block diagram of an example embodiment of an Automated Polynucleotide Synthesis Design System.

FIG. 1 is an example block diagram of an example embodiment of an Automated Polynucleotide Synthesis Design System. The example APSDS 100 comprises user interface support 102, a synthesis design engine 103, a synthesis rule data repository 105, and a synthesis data repository 104. Through the user interface support 102, the APSDS communicates with clients 101 to specify configurable parameters to the synthesis design process, such as a specification of a desired target DNA sequence and/or control parameters that affect the synthesis design process, such as desired oligo length. In one embodiment, the user interface support 102 provides a secure web-based client interface over, for example, a network such as the Internet. One skilled in the art will recognize that embodiments of the present invention are intended to work with any physical configuration, distributed, local, wireless, or otherwise, that could host one or more parts of the APSDS. The synthesis design engine 103, as will be explained in further detail below, receives a target DNA sequence specification from the user interface support 102 and, using the rules stored in the synthesis rules data repository 105, generates a synthesis design, which is then stored in the synthesis data repository 104. The synthesis design comprises sufficient data to drive a synthesis process using a particular ligation technique. For example, the design may define the set of oligos (and fragments) that need to be synthesized and the order in which they should be ligated to correctly generate the target sequence(s). The synthesis rules contained in the synthesis rules data repository 105 that are used to drive the synthesis design engine 103 may or may not be dependent upon the type of synthesis being used. For example, the criteria used to examine a potential synthesis design to determine whether correct or incorrect ligations will occur are stored in repository 105. In addition, criteria that are only applicable when using particular types of synthesis techniques may be also stored in repository 105. In one embodiment, the synthesis design engine 103 directly or indirectly controls instruments 107, such as oligo synthesizers that carry out the synthesis process, through instrument control systems 106. This may be accomplished, for example, by generating the appropriate instrument-specific commands automatically as part of the design, or under a separate user interface, or by communicating through another software module, such as a scheduling and synthesis control module, potentially provided by another supplier.

Figure 2:
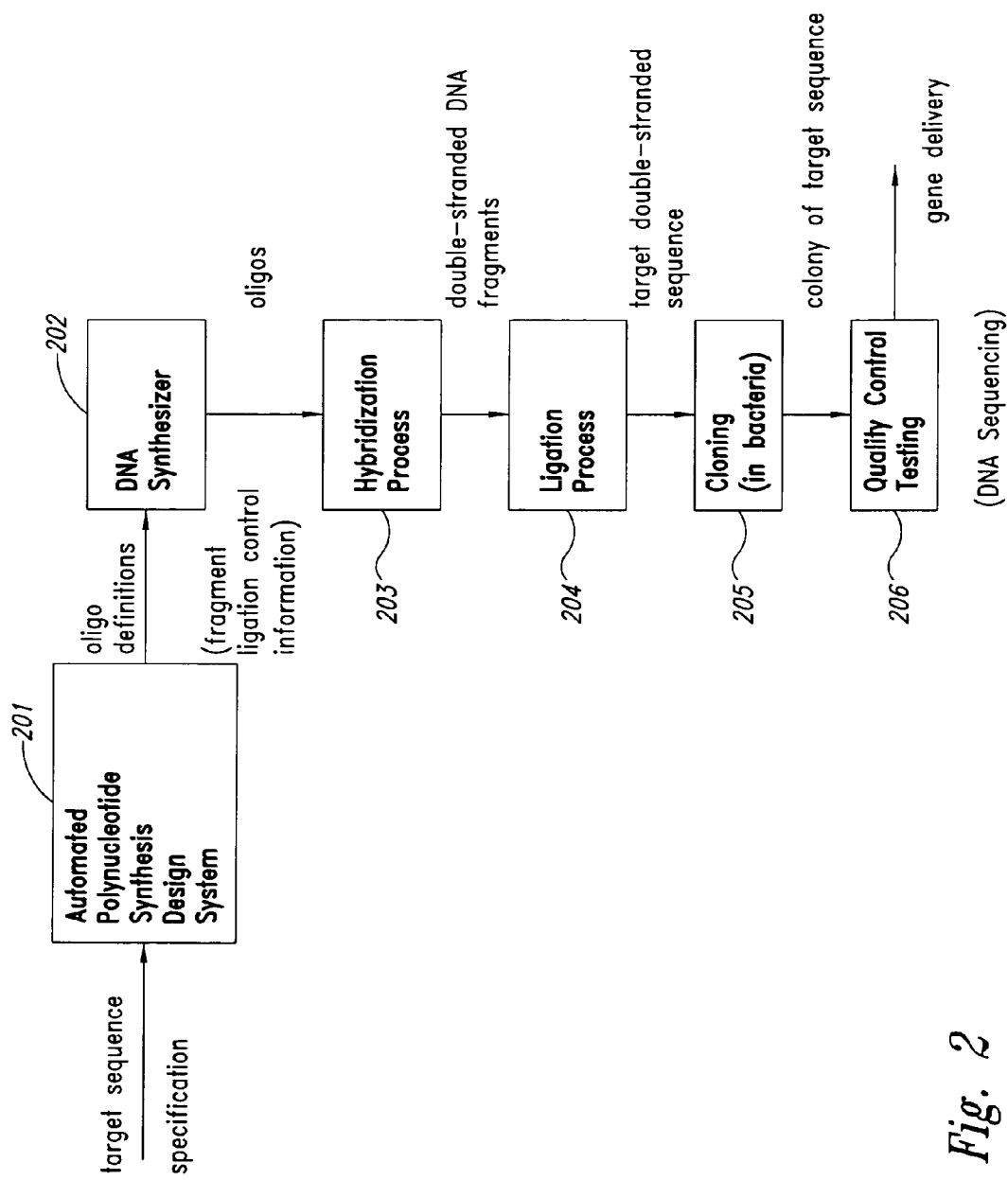
FIG. 2 is an example block diagram of a gene synthesis process that incorporates an example Automated Polynucleotide Synthesis Design System of the present invention.

FIG. 2 is an example block diagram of a gene synthesis process that incorporates an example Automated Polynucleotide Synthesis Design System of the present invention. In FIG. 2, a specification of a target sequence(s) for which a synthesis design is to be generated is supplied to the APSDS 201. The APSDS 201 automatically generates a synthesis design according to the techniques of the present invention, which are further described below. Part of the generated design is a specification of the oligos that need to be synthesized. These oligo definitions are fed to a DNA sequence synthesizer 202, for example a Beckman Oligo 1000M synthesizer, which synthesizes oligos. The oligos are then placed into storage and/or reaction vessels, e.g., 96-well plates. The synthesized oligos are then subjected to a hybridization process 203, whereby selected oligos are combined into pairs and allowed to form hybrids, i.e., form the double-stranded DNA fragments indicated by the synthesis design that was generated by the APSDS 201. These double-stranded DNA fragments are then subjected to a ligation process 204, whereby DNA fragments are combined in the presence of a ligase in an order specified by the synthesis design that was generated by the APSDS 201 to generate a desired DNA fragment that satisfies the target sequence(s). The order of ligation reactions is dependent upon the synthesis (ligation) technique (scheme) being used and the ligation process 204 supports ligations of pairs or groups of fragments ligated in a hierarchical or iterative fashion to create longer and longer fragments. The ligation process 204 is repeated as needed to provide the target double-stranded sequence. Once the target double-stranded sequence has been synthesized, the sequence is cloned by a cloning process 205 to produce colonies of the target sequence in bacteria. Samples of these colonies are then checked, for example by DNA sequencing, by the quality control testing process 206 to insure correct sequences have been produced. Once verified, the synthesized sequences (the genes) are delivered to the requesting client.

Figure 3:
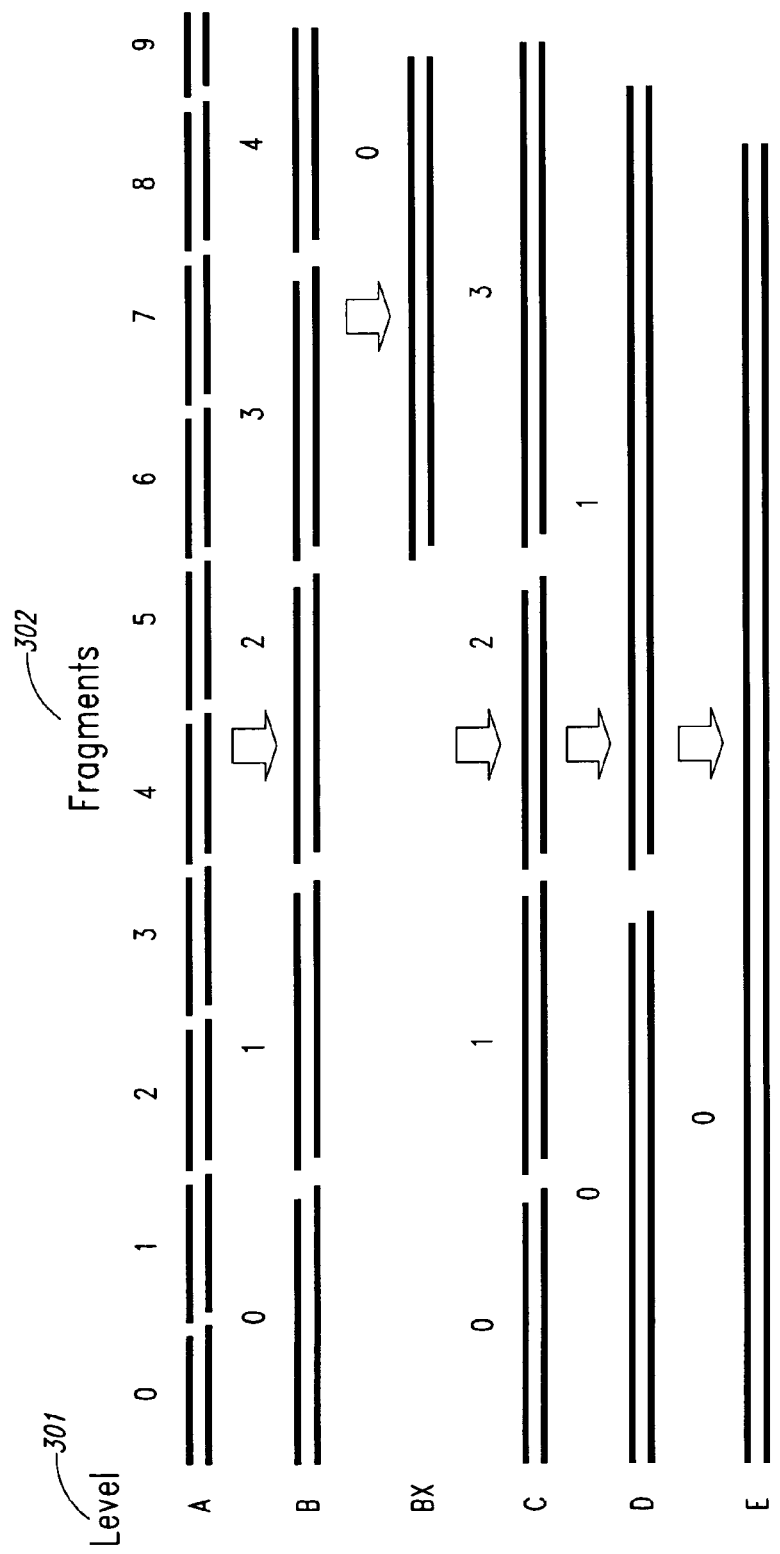
FIG. 3 is an example schematic diagram of convergent synthesis technique.

When the gene synthesis procedure of FIG. 2 uses a convergent synthesis process, then the ligation process 204 progressively generates larger and larger DNA fragments from pairs of smaller fragments until the target sequence(s) is generated. FIG. 3 is an example schematic diagram of the convergent synthesis technique. In FIG. 3, multiple levels 301 of combining double-stranded fragments 302 (a hierarchy of levels) are shown as Levels A–E. Pairs of fragments on a particular level are ligated to produce the fragments of the next higher level. Specifically, pairs of fragments from Level A are ligated to produce the fragments needed for Level B. Pairs of fragments from Level B are then ligated to produce the fragments needed in the next higher level, and so on, until there are no more fragments to combine. (See, for example, Level E.) In one embodiment, the initial fragments to be used (the fragments of Level A) are determined by dividing the target sequence into polynucleotide sequences of a designated oligo length. Other initial configurations are possible.

In practice, two complications occur with convergent synthesis. First, whenever the number of initial fragments is not a power of two, then, at some level, there will be generated an odd number of fragments. For example, in FIG. 3, there are 5 fragments, labeled with numbers 0–4, created at Level B. One skilled in the art will recognize that several techniques can be used to handle the "extra" fragment. In one such technique, an additional level (see, for example, Level BX) is added to pair-wise ligate the two rightmost fragments first (e.g., fragments 3 and 4) and then that product fragment is used as the rightmost fragment in the next level (see, e.g., fragment 3 of Level C). Another technique is to consolidate all extra fragment ligations on a single level so that successive ligation levels produce only a number of fragments that is a power of two. Other similar techniques and variations thereof are also possible.

Figure 4:
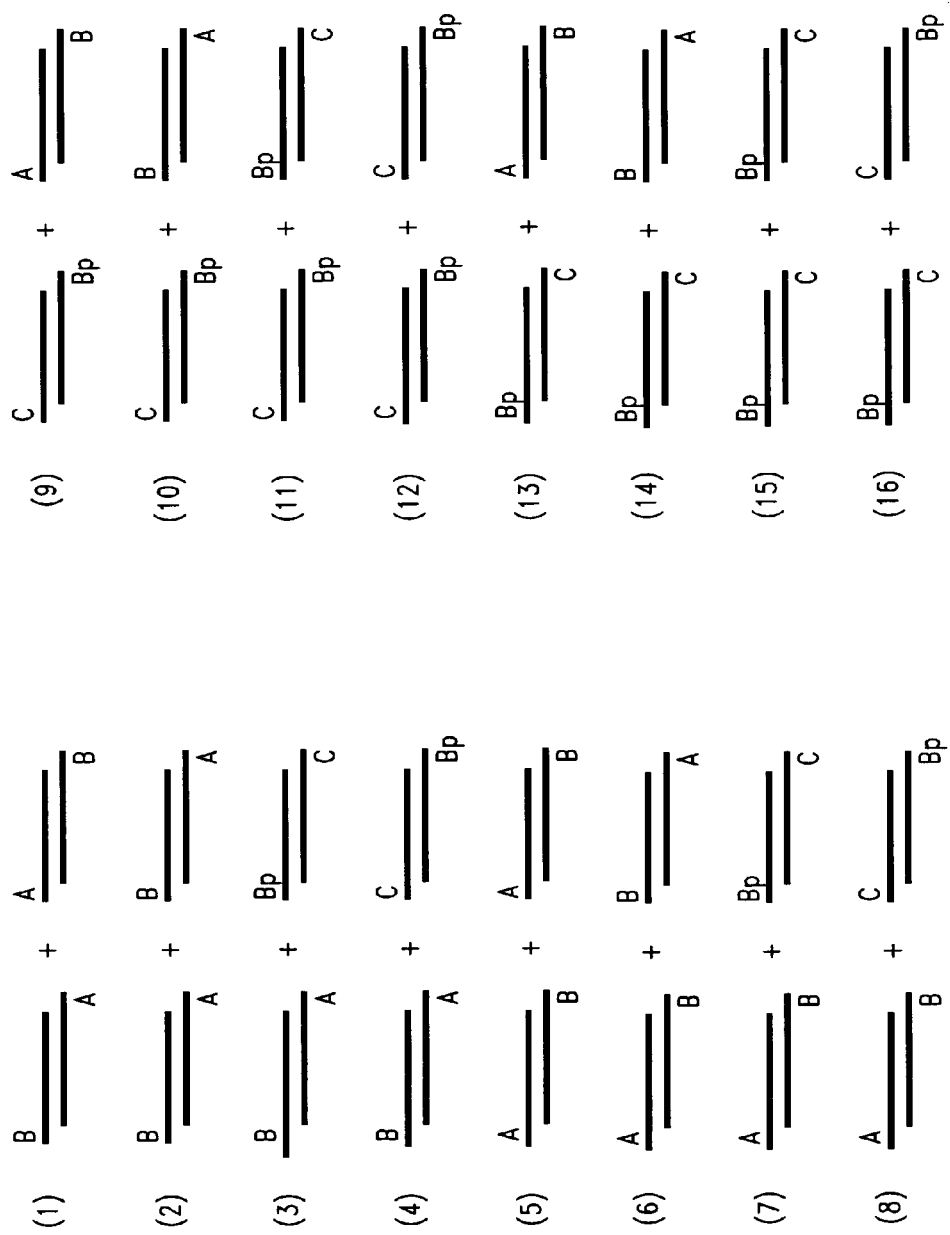
FIG. 4 is an example illustration of an interference problem caused by ligating a pair of fragments.

Second, for every pair of DNA fragments involved in a ligation reaction, the synthesis process needs to insure that each fragment combines (ligates) properly with the other fragment so as to produce only correct ligations. Since each fragment potentially has two (overhanging) ends, the synthesis process needs to insure that each end of the two ends will only ligate with the desired end of another fragment. In the laboratory, since large numbers of DNA molecules participate in each ligation reaction, all possible combinations of ends will potentially ligate. This is termed the "interference problem," since undesired ligations can interfere with synthesis of a correct sequence. Because each pair of fragments has 4 ends, these ends can potentially combine in 16 (10 different) ways as illustrated in FIG. 4, discussed below. When any two such ends are exactly complementary, they will tend to ligate (other conditions being equal), whether such ligation is desired or not. Thus, the design process needs to insure that only one combination of the four ends will combine.

For example, given two shorter DNA fragments:

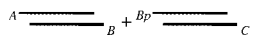

the synthesis process needs to insure that the fragments will ligate only in one way to produce the new desired fragment:

The base sequences of the four overhanging ends of the pair of shorter DNA fragments are denoted by an "A," "B," Bp," and "C." The first fragment has end sequences denoted by an "A" (top) and a "B" (bottom), and the second fragment has end sequences denoted by a "Bp" (top) and "C" (bottom). (The second fragment is written 5' to 3' per convention and thus the top and bottom strand are reversed.) The "Bp" sequence of the left end of the second fragment indicates the fact that the overhang of the left end of the second fragment is the exact complement of the overhang of the right end of the first fragment (reverse complement when written 5' to 3', as per convention). In this case, the desired reaction ligates the "B" and "Bp" ends to form a longer fragment with end sequences denoted by the "A" and the "C."

FIG. 4 is an example illustration of an interference problem caused by ligating a pair of fragments. FIG. 4 illustrates 16 possible ligations that can occur with the pair of fragments shown above, only one of which is desired, the combination of ends "B" and "Bp." In the first, second, fifth, and sixth reactions, a first fragment incorrectly ligates with a copy of itself. Similarly, in the eleventh, twelfth, fifteenth, and sixteenth reactions, a second fragment incorrectly ligates with a copy of itself. The other reactions represent ligations of the first and second fragments that are undesired with the exception of the seventh reaction:

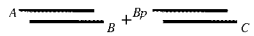

For correct ligation to be possible, the overhang types (5' or 3') must be the same; the overhang lengths must be the same; and the overhangs in the top and bottom strands must be exactly complementary. To complicate matters, empirical evidence used with the present invention has demonstrated that ligations can occur even when the ends of the two fragments are not exactly complementary and even when the overhang lengths are not the same. Specifically, there are instances in the laboratory wherein two ends behave as though they are exactly complementary. This behavior is referred to herein as "approximately complementary;" that is, an end is approximately (or effectively) complementary to another end if it behaves as though it is exactly complementary in a ligation reaction.

Laboratory experiments have shown that certain conditions will tend to generate approximate complementarity. One skilled in the art will recognize that other conditions may be demonstrated empirically, and that such conditions can easily be incorporated into synthesis rules used to determine whether two ends will ligate correctly. However, as described above in connection with FIG. 4, for a ligation composed of two fragments, there are 10 potential ligation products. The only correct product is ligation reaction 7. Ends that are designed using strict Watson Crick complementarity where A binds T and C binds G are insufficient to predict incorrect ligations. In order to discover non-Watson-Crick base pair interactions that result in non-specific ligations we have tested thousands of different combinations of ends have been tested and these results translated into rules for an algorithm used to design gene synthesis strategies.

The nine incorrect ligation reactions shown in FIG. 4 can be divided into two types based on the type of products that are formed: ligation reactions that form incorrect products that are equal in length to two fragments (see the type 1, 6, 11 and 16); and ligation reactions that form incorrect products that are polymers whose lengths are multiples of 3 or more times the length of the fragments (see the types 2/5, 3/9, 4/13, 8/14 and 12/15). All the products, including the correct product, are distinguishable using ligation reactions containing both fragments (normal ligation) or ligation reactions with one fragment (self ligations) with length analysis by polyacrylamide gel electrophoresis (PAGE).

It is desirable to perform an analysis to identify fragments that form incorrect products that are equal in length to two fragments. The test for this type of incorrect ligation is to set up two ligation reactions with only one fragment present in each ligation (self ligation test). There are three potential outcomes from this type of ligation experiment. (1) If the ends are specific, as is the case for ligation reaction 7/10, or non-specific as is the case for the ends of the type similar to 8/14, 4/13 or 3/9, then no ligation product will result. (2) If the ends are of the type similar to ligation reactions 1, 6, 11 and 16, then a ligation product equal in length to two fragments will result. (3) If the ends are of the type similar to ligation reactions 2/5 or 12/15, then any products are polymers whose lengths are multiples of 3 or more time the length of the fragments.

In is also desirable to perform an analysis to identify fragments that form incorrect ligations composed of multiple fragments. The test for this type of incorrect ligation is to set up a standard ligation reaction with two fragments. There are two potential outcomes for this ligation. (1) If the ends are specific, as is for ligation reaction 4/13, or non-specific as is for the ends of the type similar to ligation reactions 6, 1, or 16, then a single product will result. (2) If the ends are of the type similar to ligation reactions 2/5, 8/14, 7/10, 3/9 or 12/15, then multiple products will result.

From the two self ligation and single normal ligation experiments described above, ends can be classified as follows:

Specific ends: If the self ligation reactions have no ligation product and the normal ligation reaction has a single ligation product, all four ends involved are specific with respect to one another. If a self ligation reaction has no ligation products then the ends of the fragment are specific with respect to one another.

Non-specific ends: If the self ligation has no ligation products and the normal ligation has multiple products the end(s) in one fragment interact with end(s) in the other fragment. If the self ligation reaction has one ligation product and the normal ligation has a single ligation product the fragment has one end that is non-specific and reacts with itself. If both self ligation reactions have one ligation product and the normal ligation reaction has one ligation product then the two ends that join the fragments are non-specific with themselves. If the self ligation reaction has multiple ligation products the joints in the fragment are interacting with themselves and/or each other.

Thousands of ends have been evaluated using the strategy described above. The results of these experiments have been compiled and stored in a data repository. The specificity of each end with itself and other ends is recorded. This information is analyzed to build the synthesis (ends-checking) rules that can be incorporated into an APSDS of the present invention.

The APSDS provides an automated solution to the interference problem by automatically designing, whenever possible, a group of fragments that can be later synthesized to create a target sequence such that no two incorrect fragment ends can join in a ligation reaction. Specifically, the APSDS generates a ligation scheme (a specific ordering of fragments and ligation reactions) that insures, wherever possible, that only desired ligations will succeed. In some embodiments, different designs are "scored" to indicate a level of success. Such indications are potentially useful in a laboratory setting in which tradeoffs can be made, for example, in terms of efficiency versus correctness. In summary, the APSDS examines an initial design of fragments in terms of the order in which they will be ligated, determines whether they will generate any undesired ligations (scores the design), and readjusts the fragment design and scores each readjusted design until no undesired ligations are detected.

Figure 5:
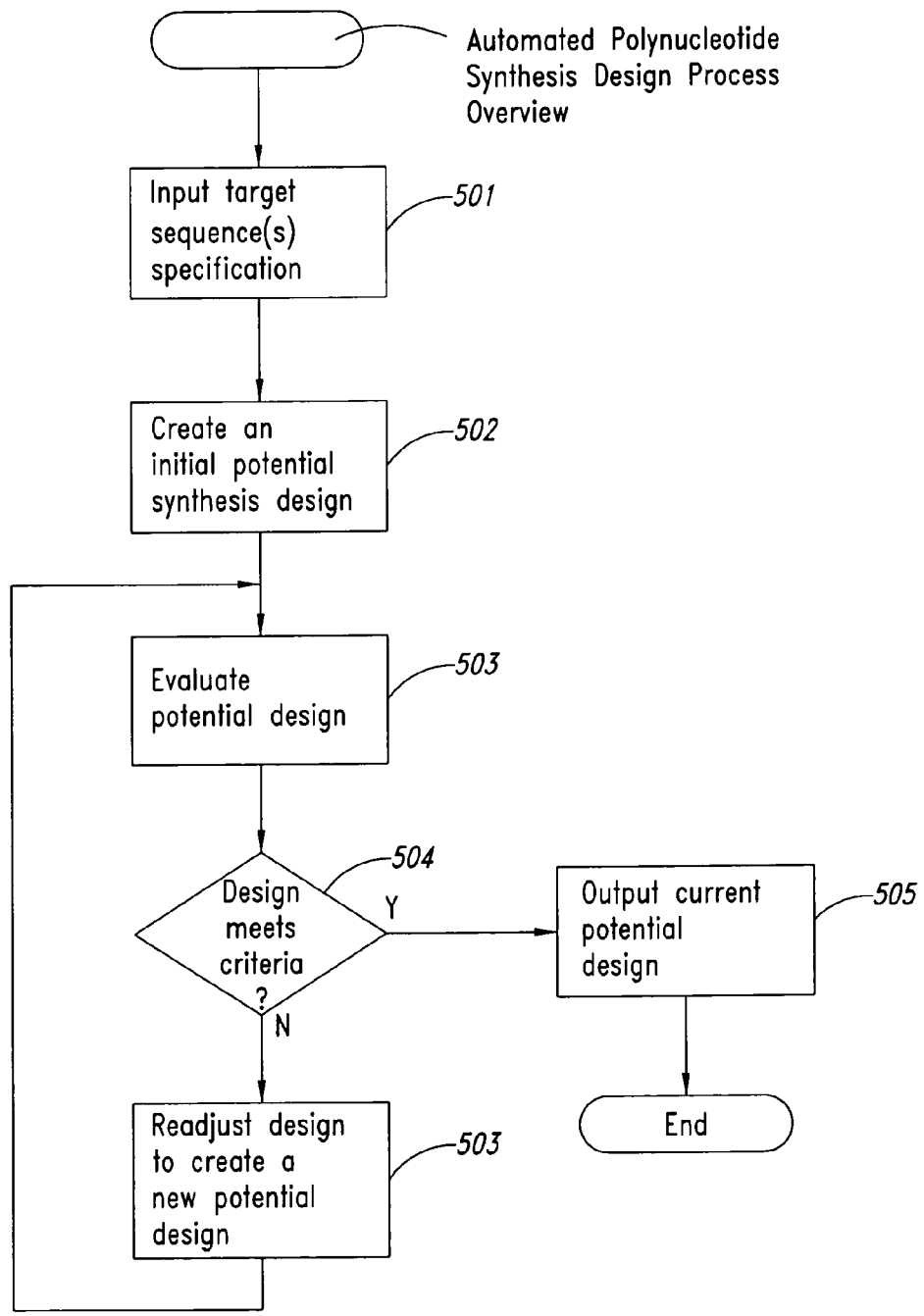
FIG. 5 is an overview flow diagram of a design process used by an example Automated Polynucleotide Synthesis Design System, which incorporates heuristics or other criteria to determine a set of fragments to synthesize independent of the synthesis technique used.

FIG. 5 is an overview flow diagram of a design process used by an example Automated Polynucleotide Synthesis Design System, which incorporates heuristics or other criteria to determine a set of fragments to synthesize independent of the synthesis technique used. In step 501, a specification of the target sequence is received by the APSDS. In step 502, the APSDS creates an initial potential synthesis design. In one embodiment, this step is performed by decomposing the target sequence (in its double-stranded form) into fragments of a length equal to a desired default oligo length. In step 503, the potential design is evaluated according to heuristics or other criteria. Such criteria may test whether a potential design minimizes the occurrence of incorrect ligations that may result from the fragments specified in the potential design. In one embodiment, the evaluation criteria determine whether the ends involved in each potential ligation reaction will ligate as desired. These ligation rules are preferably empirically based upon results determined in a laboratory. In some embodiments, the evaluation criteria determine whether fragment ends will properly ligate by checking for approximate complementarity as well as exact complementarity. In addition, new or modified evaluation criteria preferably can be dynamically added to the system. In other embodiments, the criteria may be used to evaluate aspects of a potential design other than those that are ligation related. In addition, the evaluation process may provide an indication, such as a score, of the relative success of the potential design. One skilled in the art will recognize that many variations are possible. In step 504, the APSDS determines whether the potential design meets the specified criteria, and, if so, continues in step 505, else continues in step 506. In step 505, the (now successful) potential design is output, and the process ends. Alternatively, in step 506, if the potential design does not meet the criteria, then the design is adjusted to create a new potential design, and then reevaluated in step 503. In one embodiment, parameters such as a desired default oligo length, joint position, overhang type, and overhang length can be varied and adjusted to change the specification of the fragments (the potential design). One skilled in the art will recognize that other parameters may be incorporated into the automated design procedure as they are desired. In addition, in some embodiments, a potential design, even though "unsuccessful" according to the criteria may be optionally output (not shown) along with an indication of the relative strength of that particular design. The evaluation and design adjustment process continues until the design criteria are met (or the adjustment possibilities are exhausted).

As mentioned, in one embodiment, the APSDS evaluates (or scores) a potential synthesis design by employing "ends-checking rules" to test whether all combinations of possible interference reactions will succeed. The ends-checking rules account for the possibility of approximate complementarity of ends generating incorrect ligations, as well as other empirical rules that may cause incorrect ligations to occur in practice. In one embodiment, the ends-checking rules determine whether a pair of ends are:

(1) exactly complementary using Watson-Crick traditional base pair interactions;
(2) approximately complementary using base pairing rules empirically established (for example, "C/T" and "T/G" pairings); and/or
(3) contain "GC" components within the overhang, that is, a GC or GG or CC or CG sequence within the overhang.

In addition, partial matches (for example, 3 of 4 base pairs and 6 of 9 base pairs) of exactly or approximately complementary are also determined. Note also that different overhang lengths may empirically indicate the use of different ends-checking rules. In one embodiment, the APSDS is structured so that new ends-checking rules can be dynamically incorporated into the system, as new rules are empirically discovered or as rules need to be modified. Thus, the APSDS is designed to be extensible and dynamic as more empirical evidence for producing correct synthesis designs is discovered.

When used with convergent synthesis, the APSDS examines each potential ligation pair of fragments using the ends-checking rules and varies the specification of the fragments of the potential design until a pair of fragments is found that ligates only in the desired fashion. When used with other types of synthesis, the APSDS can be extended to search all possible combinations of ends that may arise depending upon the ordering of the ligation reactions and the number of fragments involved. For example, when used with solid phase synthesis, each fragment is successively ligated to a previous (longer) fragment that is attached to a solid support until the final fragment is produced. In this case, the left end of the fragment attached to the solid support need not be examined, but the left and right ends of the shorter fragments are examined. In another example, for other design reasons, more than two fragments may be ligated at the same time, such as in one solution where there is not an even number of fragments. In this case, the ends-checking rules are deployed against all possible combinations of the ends of the total number of fragments being examined.

FIGS. 6A–6K are example schematic diagrams of the fragments tested and adjusted at each level in an example APSDS used to generate a convergent synthesis design. In summary, convergent synthesis builds up a long polynucleotide sequence by successively ligating pairs of fragments, and then ligating, by pairs, the products of those reactions and then ligating. In order to build a design for convergent synthesis that will ligate as desired, the techniques used by the APSDS successively check the ligatability of each pair of "potential" fragments, beginning with the longest (target) sequence, and working "backwards" to fragments of a length that approximates the default desired oligo length. (The technique uses a binary decomposition approach.) The APSDS modifies a pair of fragments (thereby adjusting the joint) when the ligatability index indicates that the potential fragments will not ligate according to designated criteria. One skilled in the art will recognize that whether one discusses the adjustments in terms of fragment definitions (attributes) or in terms of the joint itself does not affect the functionality of technique—a change in one will necessarily affect the other.

Figure 6A:
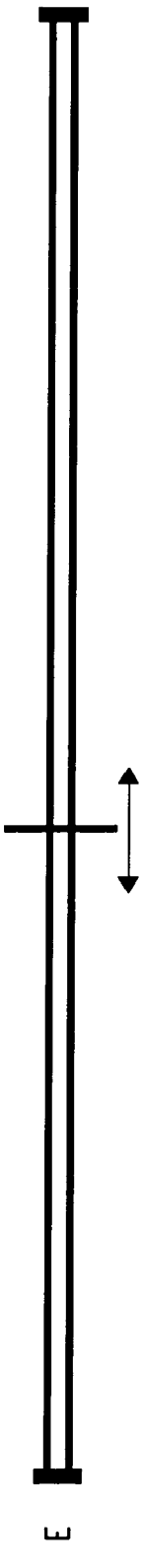

Specifically, as can be observed in FIG. 3, the example target sequence denoted as Level E is divided initially into 10 fragments (9 fragments of size desired oligo length and a $10^{th}$ fragment of the remaining portion of the sequence). These initial "potential" fragments are then tested for proper ligatability and adjusted as needed according to a protocol (i.e., in an order) discussed relative to FIGS. 6A–6K. In FIGS. 6A and 6B, the APSDS examines the joint between the two potential fragments that currently constitute Level D. The APSDS examines the ends that may ligate in constructing this joint, evaluates the synthesis criteria, and if the evaluation indicates success, then the APSDS establishes that the next largest fragment (the "fragment" of Level E) will synthesize properly and thus includes Level D, and potential fragments 0 and 1 in the resultant synthesis design. For purposes of examining the next level, the joint between Level D fragments 0 and 1 is considered frozen.

Figure 6C:
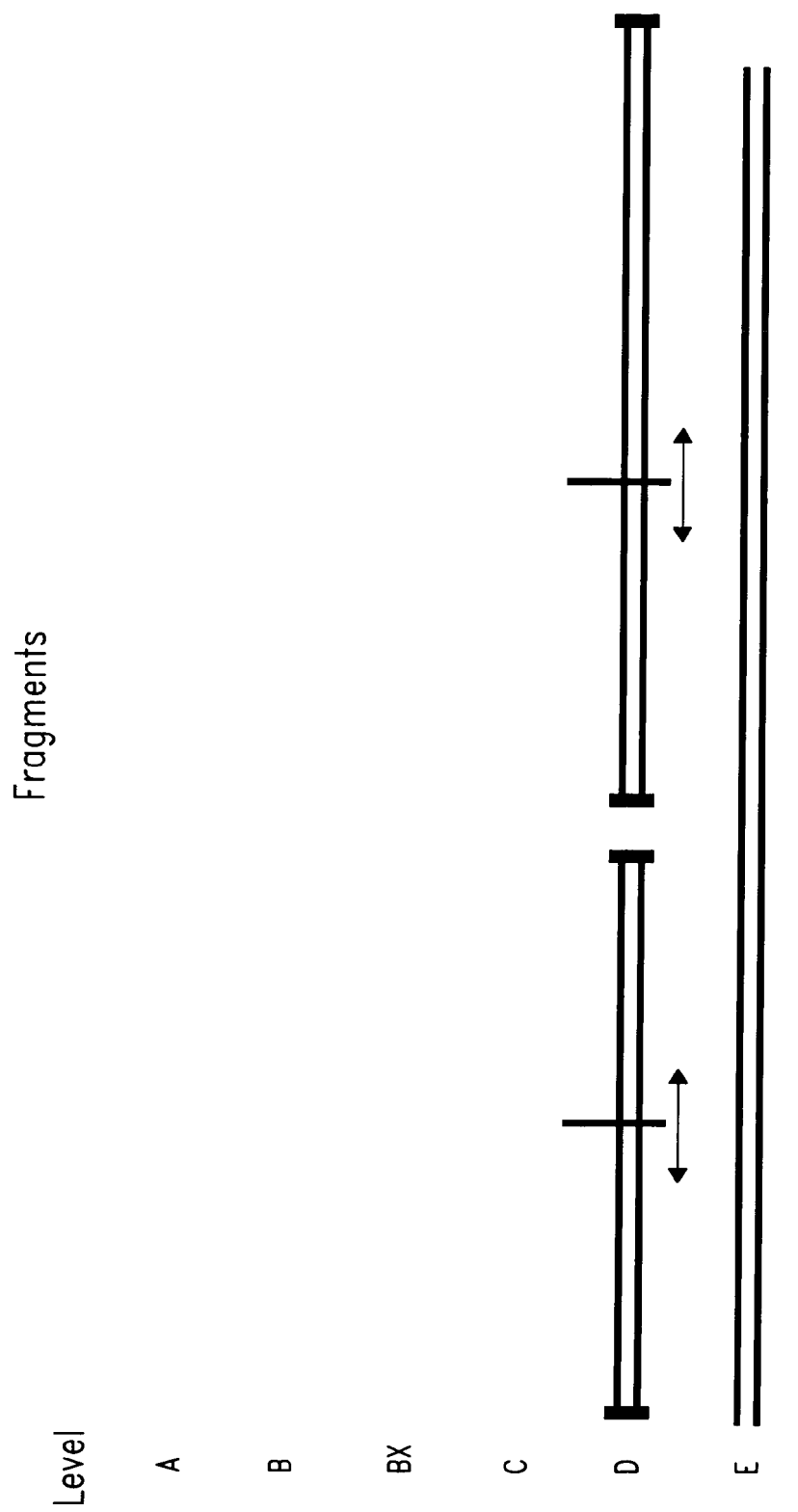
Figure 6D:
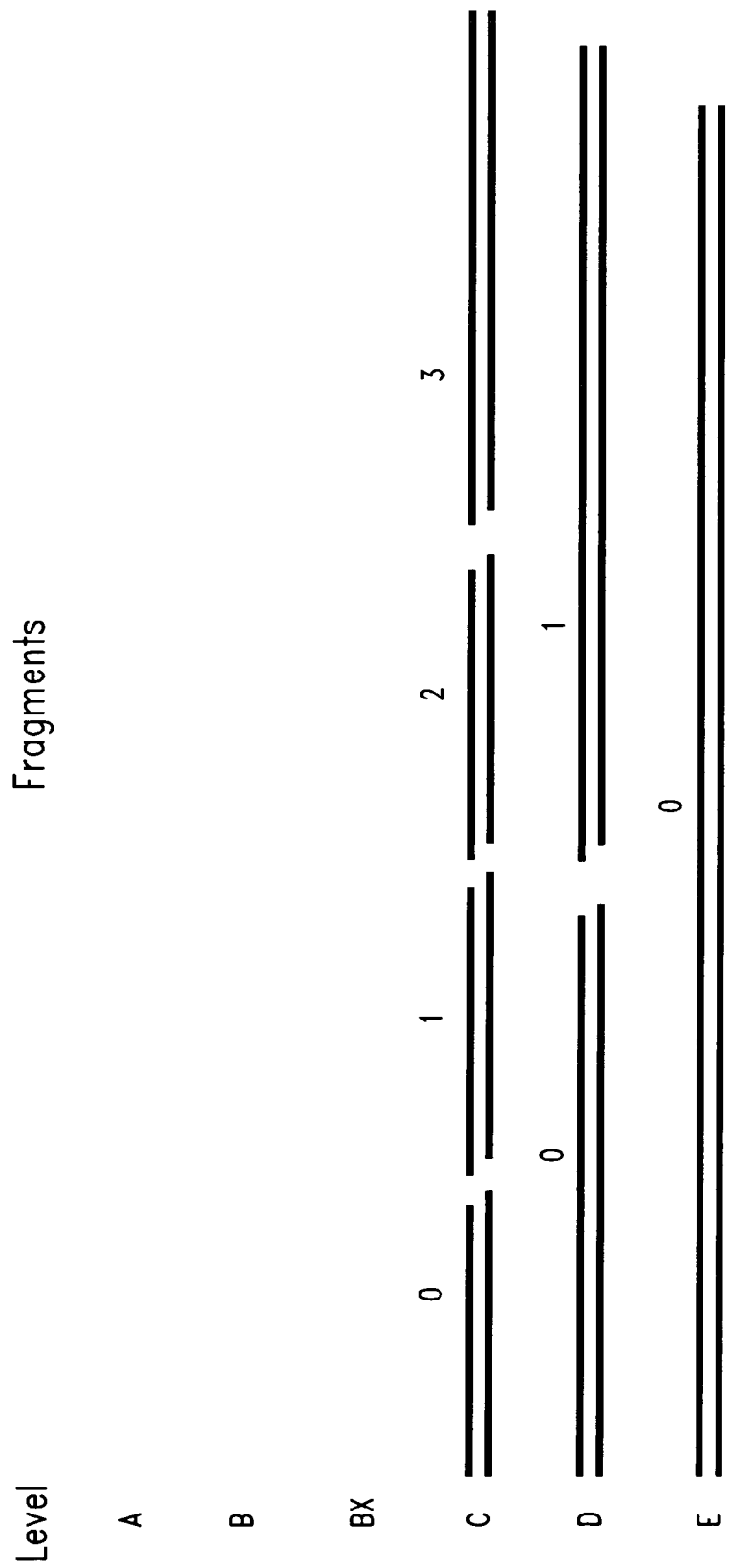

Similarly, in FIGS. 6C and 6D, the APSDS examines the ends that contribute to constructing a joint between potential fragments 0 and 1 of Level C and the ends that contribute to constructing a joint between potential fragments 2 and 3 of Level C, according to the synthesis criteria. If the synthesis criteria indicate that one of these joints will not be successful, then in FIG. 6C the joint is adjusted. As mentioned, in one embodiment the joint adjustment consists of changing the overhang type of the joint or moving the joint position left or right (thus changing the fragment definitions). Once the synthesis criteria indicate that the joints will successfully ligate at this level, the APSDS establishes that these next largest fragments (the fragments of Level D) will synthesize properly and thus includes Level C, and potential fragments 0, 1, 2 and 3 in the resultant synthesis design. The design constructed thus far is shown in FIG. 6D. For purposes of examining the next level, the joints between fragments 0 and 1 and fragments 2 and 3 of Level C are considered frozen.

Figure 6E:
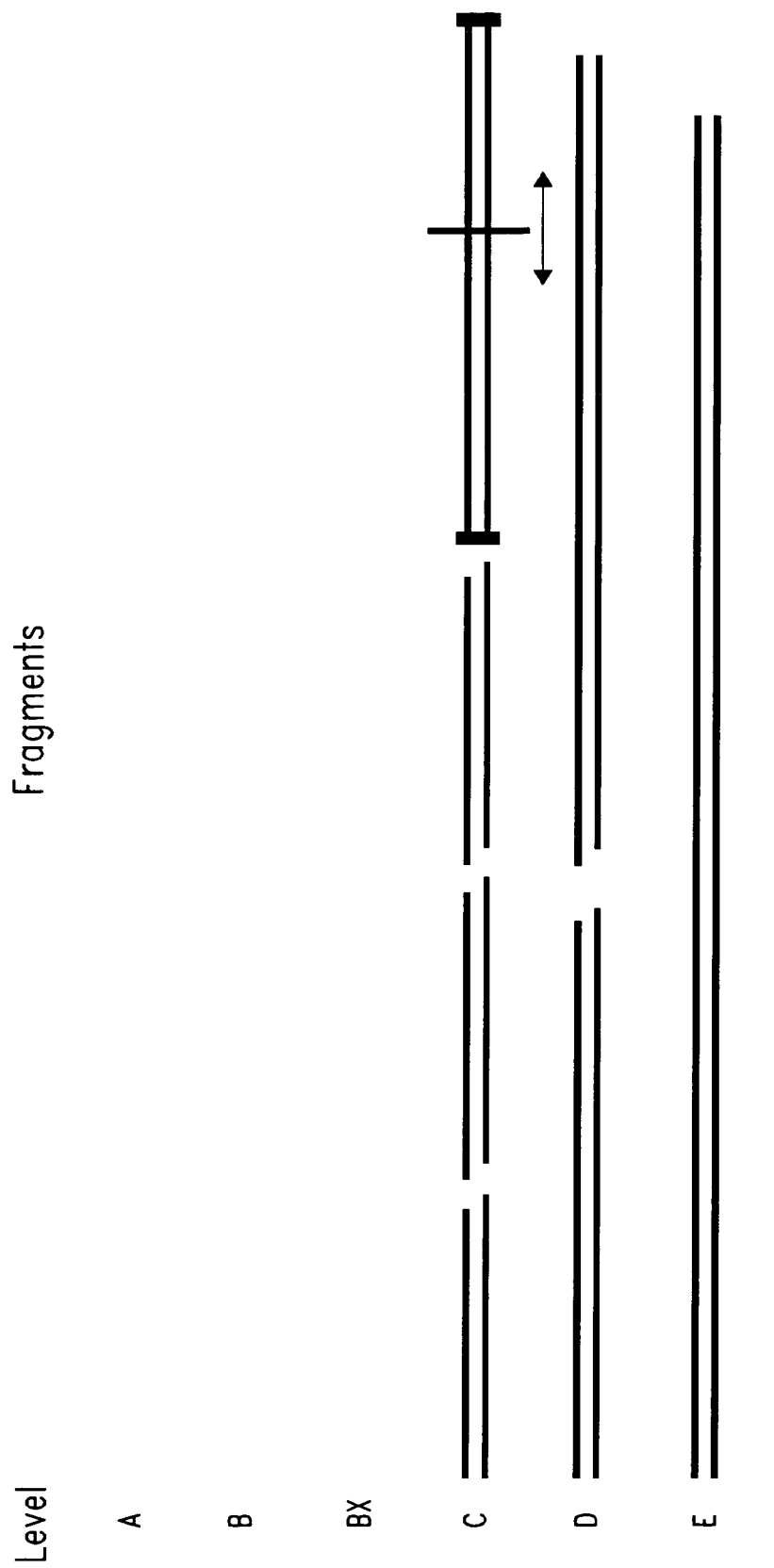
Figure 6F:
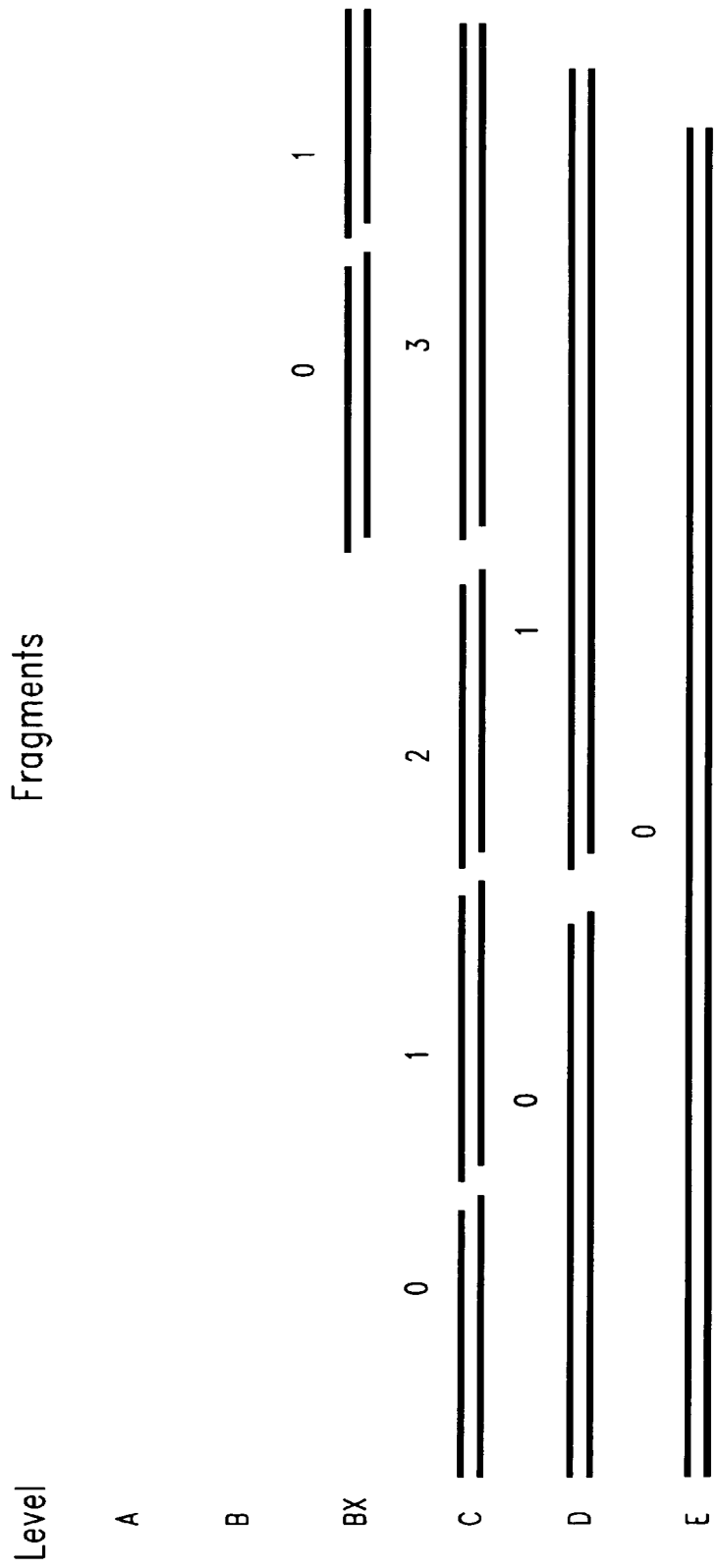
Figure 6G:
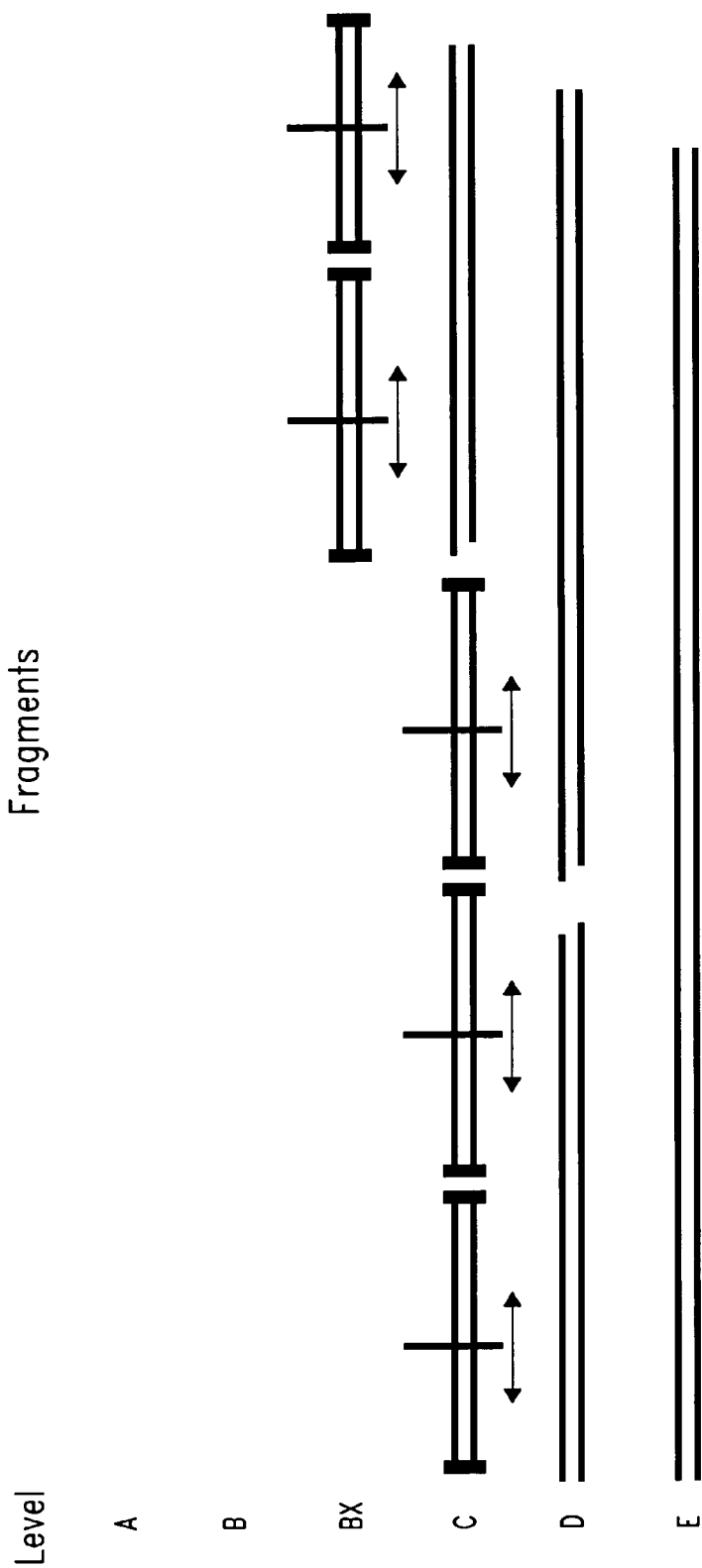
Figure 6H:
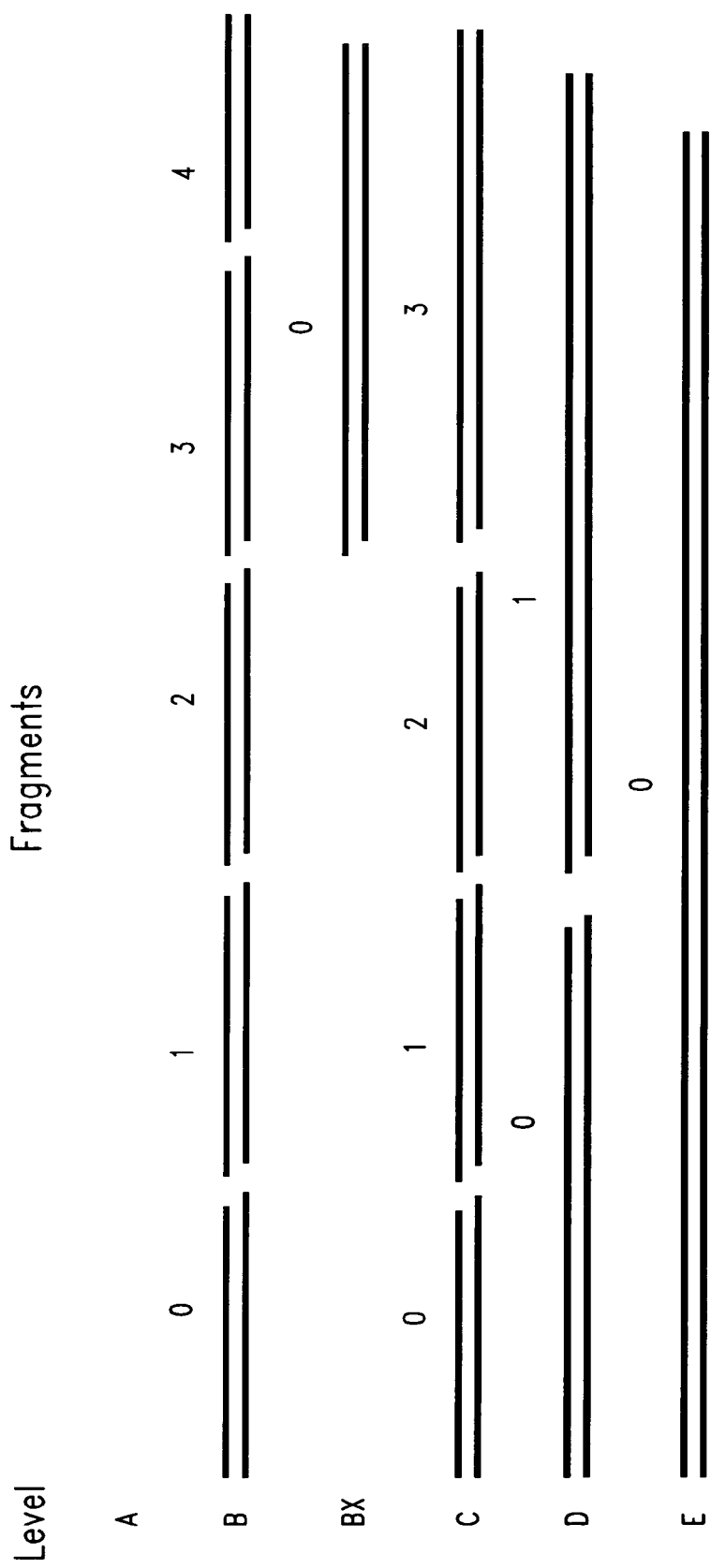
Figure 6I:
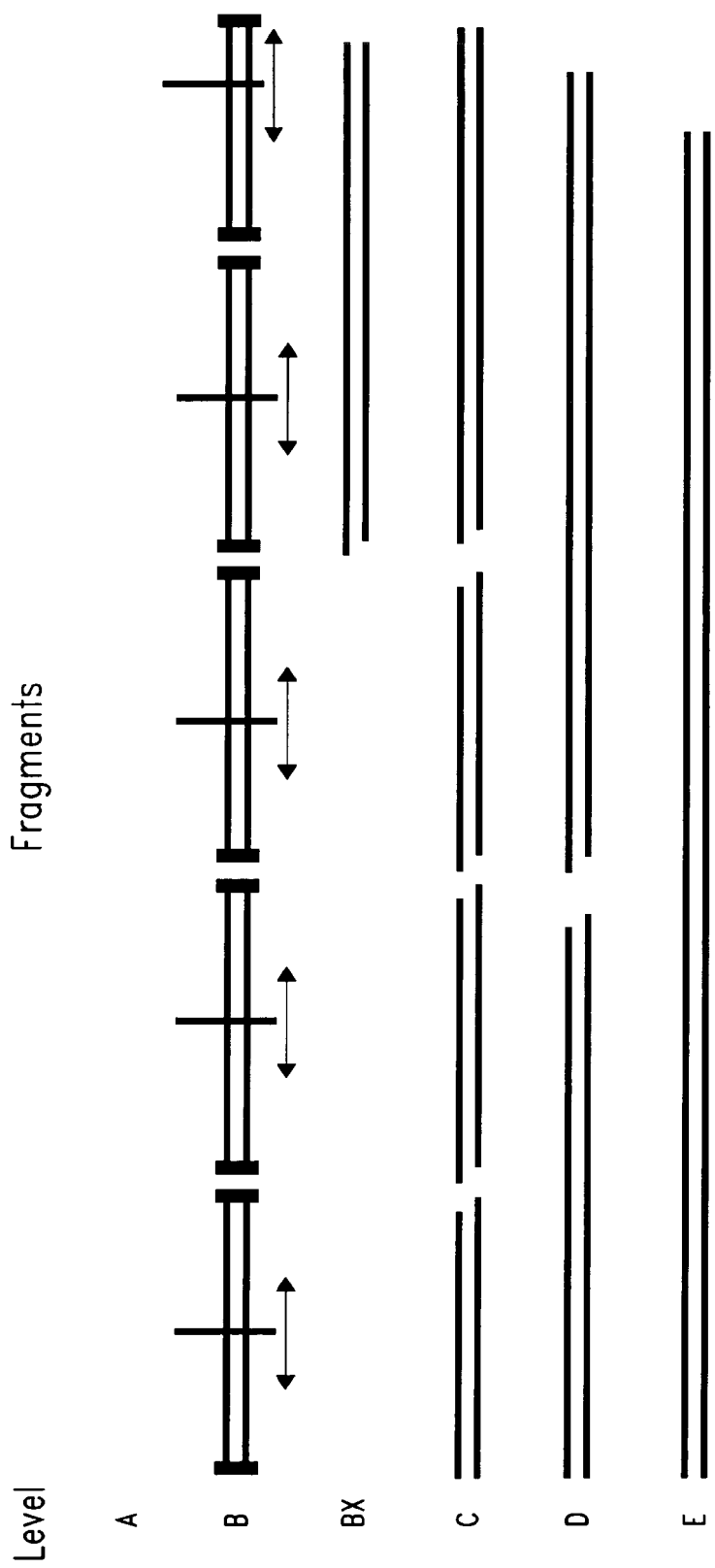
Figure 6J:
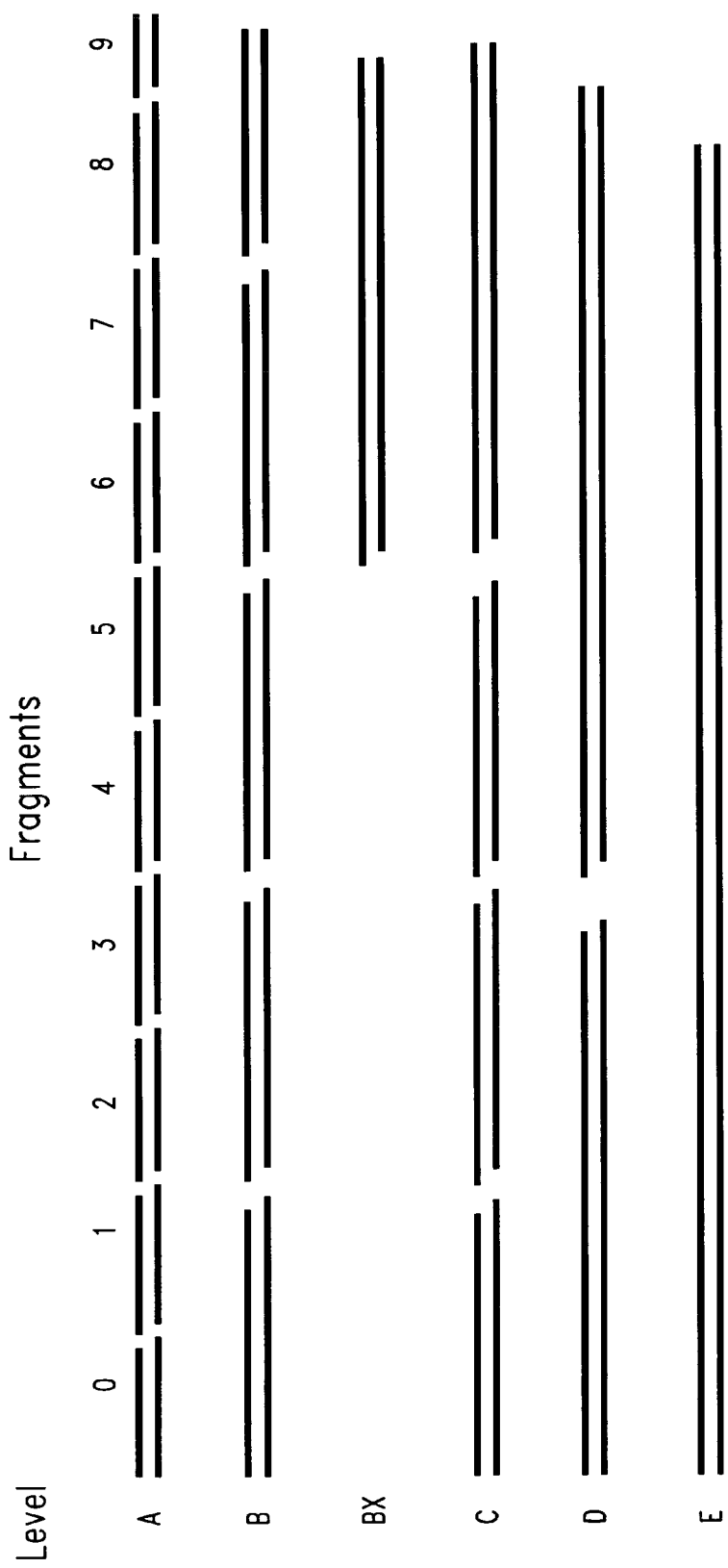
Figure 6K:
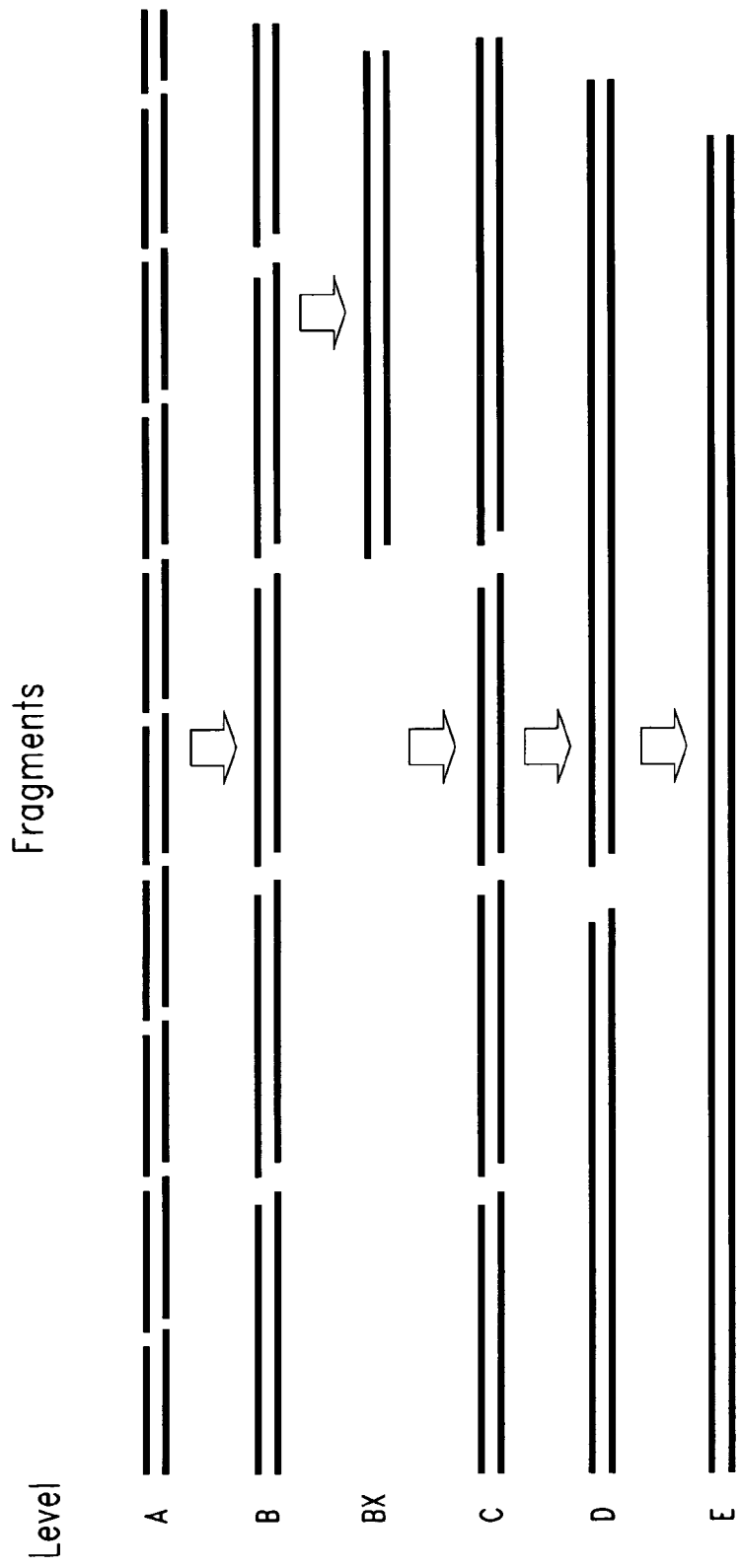

In a similar fashion, the joints between the potential fragments of the remaining levels are examined, evaluated, and adjusted until the synthesis criteria indicates that a potential fragment pair meets the synthesis criteria and should be included in the design. FIG. 6E shows the evaluations and adjustments made to create Level BX; and FIG. 6F shows the resulting intermediary design including the fragments of Levels E through BX. FIG. 6G shows the evaluations and adjustments made to create Level B; and FIG. 6H shows the resulting intermediary design including the fragments of Levels E through BX. FIG. 6I shows the evaluations and adjustments made to create Level A—the smallest fragments to be synthesized, from which the oligo designs are taken. FIGS. 6J and 6K shows the resulting design including the fragments of Levels E through A. FIG. 6K shows the ordering of the ligations that will need to be performed to synthesize the polynucleotide sequence denoted by Level E.

Figure 7:
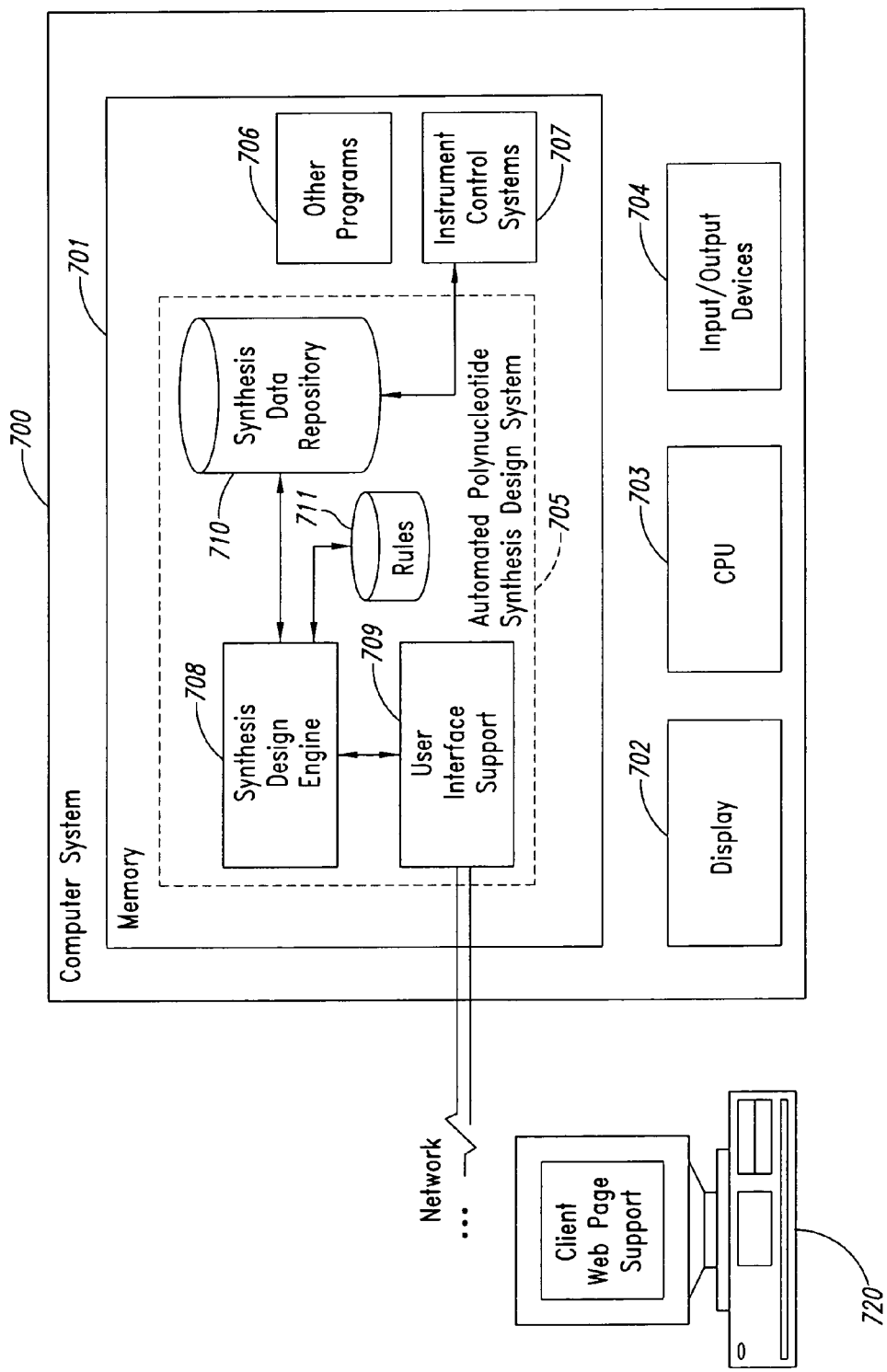
FIG. 7 is a block diagram of a general-purpose computer system for practicing embodiments of the Automated Polynucleotide Synthesis Design System.

FIG. 7 is a block diagram of a general-purpose computer system for practicing embodiments of the Automated Polynucleotide Synthesis Design System. The computer system 700 contains a central processing unit (CPU) 703, a display 702, a computer memory (memory) 701, or other computer-readable memory medium, and other input/output devices 704. The components of the APSDS 705 typically reside in the memory 701 and execute on the CPU 703. As described in FIG. 1, the APSDS 705 comprises various components, including a synthesis design engine 708, user interface support 709, a synthesis rules repository 711, and a synthesis data repository 710. These components are shown residing in the memory 701. As also described, the APSDS 705 may be used to control instruments. Instrument control systems 707 for controlling such instruments are also shown residing in the memory 701. Other programs 706 also typically reside in the memory 701.

One skilled in the art will recognize that exemplary automated polynucleotide synthesis design systems can be implemented as one or more code modules and may be implemented in a distributed environment that is comprised of multiple, even heterogeneous, computer systems and networks. In such environments, the various programs and data repositories shown as currently residing in the memory 701 may be instead distributed among several computer systems, and communicate across a network, such as a wired network like the Internet, or over a wireless network. For example, the synthesis data repository 710, which contains the synthesize design and project data may reside on a different computer system than the computer system on which the design engine 708 resides. In addition, the synthesis design rules 705 may be stored on a remote computer system or may be combined with other synthesis data. Further, any well-known mechanism for implementing a data repository may be used to implement the data and rules repositories 710 and 711, including well-known database techniques.

As described with respect to FIG. 1, the APSDS includes a synthesis design engine 708, which automatically generates a synthesis design that meets design criteria specified by the rules contained in data repository 711 for a particular synthesis technique. In one example embodiment, the entire APSDS is implemented according to a 3-tier Java-based architecture, with the synthesis design engine 708 implemented in the Java programming language as a Java servlet. An application server is used to handle the user interface support 709 for a web-based client interface. The generated synthesis design and data structures created and stored using an Oracle database system. One skilled in the art will recognize that many other equivalent arrangements exist and would perform equally well to realize the techniques described herein.

FIGS. 8–16 describe an example embodiment of example routines within the APSDS design engine for achieving automated synthesis design capabilities using convergent synthesis techniques. One skilled in the art will recognize that these routines can be modified as appropriate to support the ligation orders dictated by using other synthesis techniques, such as for solid-phase or shotgun synthesis. Further, in example embodiments, the components of the APSDS may execute concurrently and asynchronously; thus, the components may communicate using well-known message passing techniques. One skilled in the art will recognize that equivalent synchronous embodiments are also supportable by a APSDS implementation. Also, one skilled in the art will recognize that other steps could be implemented for each routine described below, and in different orders, and in different routines, yet still equivalently achieve the functions of the APSDS.

Figure 8:
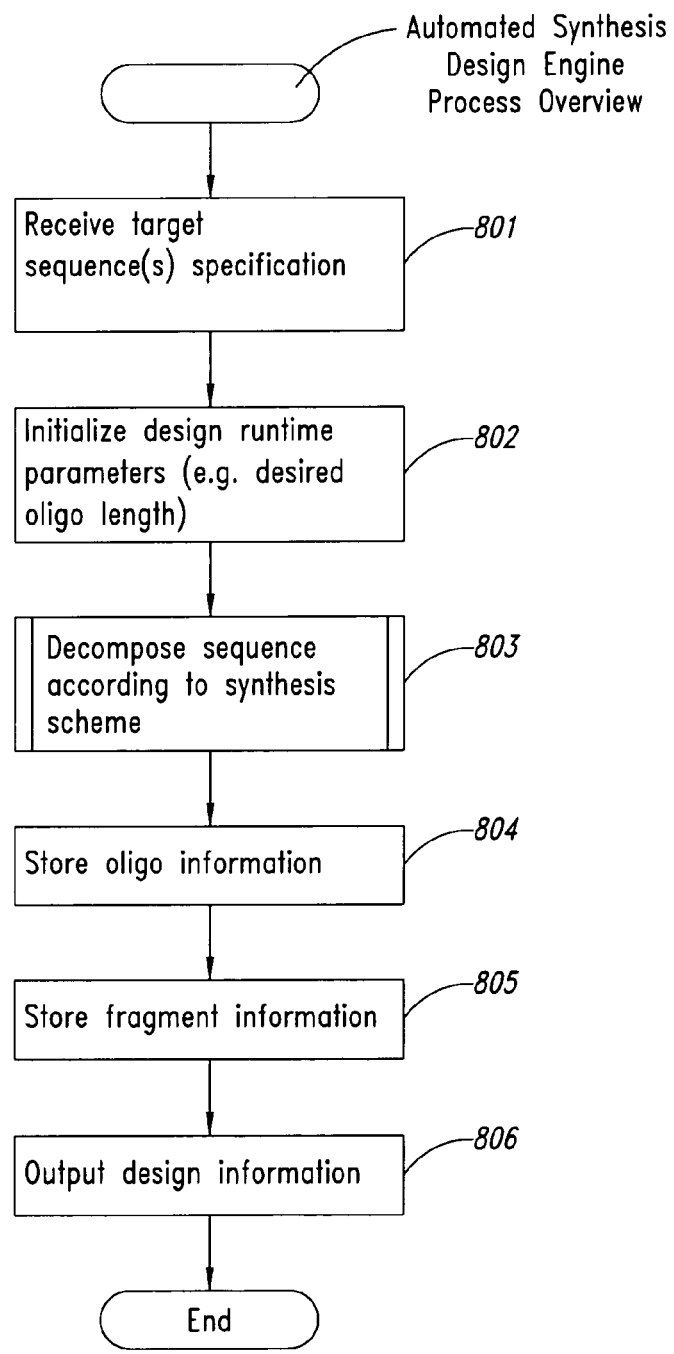
FIG. 8 is an example overview flow diagram of steps executed by an example embodiment of an automated synthesis design engine to generate a synthesis design.

FIG. 8 is an example overview flow diagram of steps executed by an example embodiment of an automated synthesis design engine to generate a synthesis design. These steps may be performed, for example, by the synthesis design engine 708 shown in FIG. 7. In step 801, the APSDS design engine receives a target sequence(s) specification. In step 802, the engine initializes synthesis design runtime parameters that can be used to control configurable aspects of the design process. For example, a user (not necessarily the client or customer) may be allowed to specify a desired (default) oligo length, default overhang type, default overhang size, type and size specifically of left ends and/or right ends, type of synthesis technique, and the ordering to apply various joint adjustment strategies. For example, the user may specify a desire to vary overhang type of the joint prior to changing a joint's position in the target sequence. In addition, in some embodiments, joints can be manually frozen. An example embodiment of an interface for providing runtime parameters is included in Appendix A, which is incorporated herein by reference in its entirety. One skilled in the art will recognize that many other configurable runtime parameters could be used with the techniques described here.

In step 803, the engine calls a routine to decompose the target sequence specification according to the designed synthesis scheme. This routine is the "workhorse" of the synthesis design process and will vary with the synthesis scheme used, because the order of ligation reactions needed will thus vary. Once the decomposition is complete, a set of fragments for generating the target sequence(s) is known as well as a build map for ligating the fragments to produce the target sequence. The decomposition routine is discussed further below with respect to FIG. 9.

In step 804, the design engine generates oligo definitions from the initial fragments of the synthesis design, and stores these oligos definitions in a data repository, such as synthesis data repository 710 in FIG. 7. (These oligo definitions are later used by the oligo synthesizer.) In some embodiments, an efficiency technique is used to attempt to speed up the synthesis process by starting the synthesis with the larger fragments from some other "level" of the design. For example, in one embodiment, the fragments of Level B are translated to oligo definitions, and these oligo definitions are the sequences synthesized by the oligo synthesizer. Depending upon the length of the fragments at the various levels, this approach may or may not be practical. Also, using this technique requires one to carefully review the ligation results to make sure that they actually worked. If they did not, then the synthesis process can fall back to using oligo definitions that correspond to the initial fragments (Level A).

In step 805, the fragment information is stored, for example, in a synthesis data repository. In step 806, design information is output to, for example, a text file, and the processing is complete. Appendix B contains an example embodiment of an output file produced by the design engine, and is herein incorporated by reference in its entirety. Depending upon needs, the output may be configured to produce information on the potential intermediary designs as the potential fragments are processed by the engine. This would allow someone to choose a "least potentially bad" solution if a particular design failed to produce a proper solution that completely satisfied the synthesis criteria. In another embodiment, command sequences for controlling a synthesizer are also output in a form to be fed to an instrument controller (or other program) that controls the synthesizer. One skilled in the art will recognize that many other possible outputs could be integrated with the design output.

Figure 9:
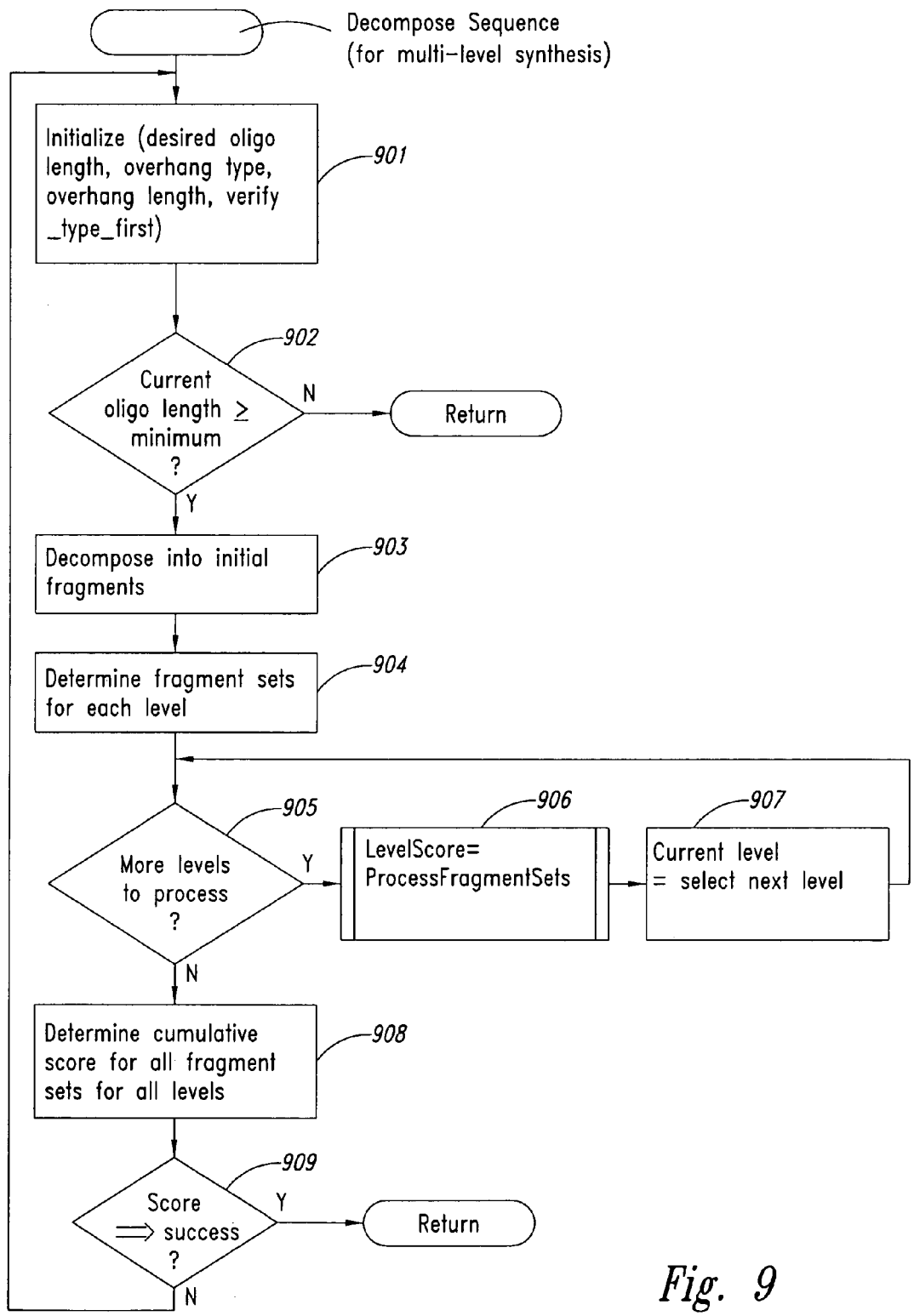
FIG. 9 is an example flow diagram of a routine for decomposing a sequence into a synthesis design.

FIG. 9 is an example flow diagram of a routine for decomposing a sequence into a synthesis design. This routine performs, for a designated target oligo length, the functions of breaking up the target design into a set of potential fragments, testing the potential fragments against the synthesis criteria, and adjusting the potential fragments until the fragments meet the synthesis criteria or no design solution is found. If no design solution is found using the designated target oligo length, then the length is changed (for example, decreased), and the process is tried again, until a design solution is found or until no more oligo lengths are permissible. Specifically, in step 901, the routine initialize various parameters such as the desired oligo length, overhang length, overhang type, and whether to adjust the overhang type prior to moving joint position, or other similar parameters. In step 902, the routine determines whether the current oligo length is permissible (for example, greater than some minimum) and, if not, returns, otherwise continues in step 903. In step 903, the routine decomposes the target sequence(s) into initial potential fragments. One technique for performing this step is to "chop" the target sequence into fragments of a length equal to the desired oligo length, with any remaining length allocated to a last fragment. For example, a target sequence of length 117 base pairs, with a desired oligo length of 25 would yield an initial set of 5 fragments of lengths {25, 25, 25, 25, 17}. The initial potential fragment definitions are then created and stored in the synthesis data repository.

In one embodiment, fragment definitions are stored as "objects" in the data repository and specify all of the information required to determine where the fragment resides in the target sequence, the actual sequence, overhang type, etc., and any other information necessary to be able to determine the overhang (end) sequences and lengths and the location of joints in the target sequence. For example, in one embodiment a fragment definition includes, for each of the top and bottom strands, indications of (1) a position in the target sequence; (2) an sequence length; and (3) a list of bases contained in the sequence. By storing the potential fragments in this manner, and by updating them as the design is constructed (for example, adjusting them to move a joint), the engine can efficiently track information and generate oligo definitions.

Once the initial potential fragments are established, the routine constructs fragment sets for each ligation level to aid in the design process. These fragment sets provide an optimization for tracking which fragment ends are participating in each potential ligation reaction (each joint) so that each group of fragments that will be ligated together can be easily evaluated against the synthesis criteria. At any point in time, the fragment sets for a joint indicate which of the smallest potential fragments (of the initial level, e.g., Level A) define the ends that need to be examined.

Figure 10:
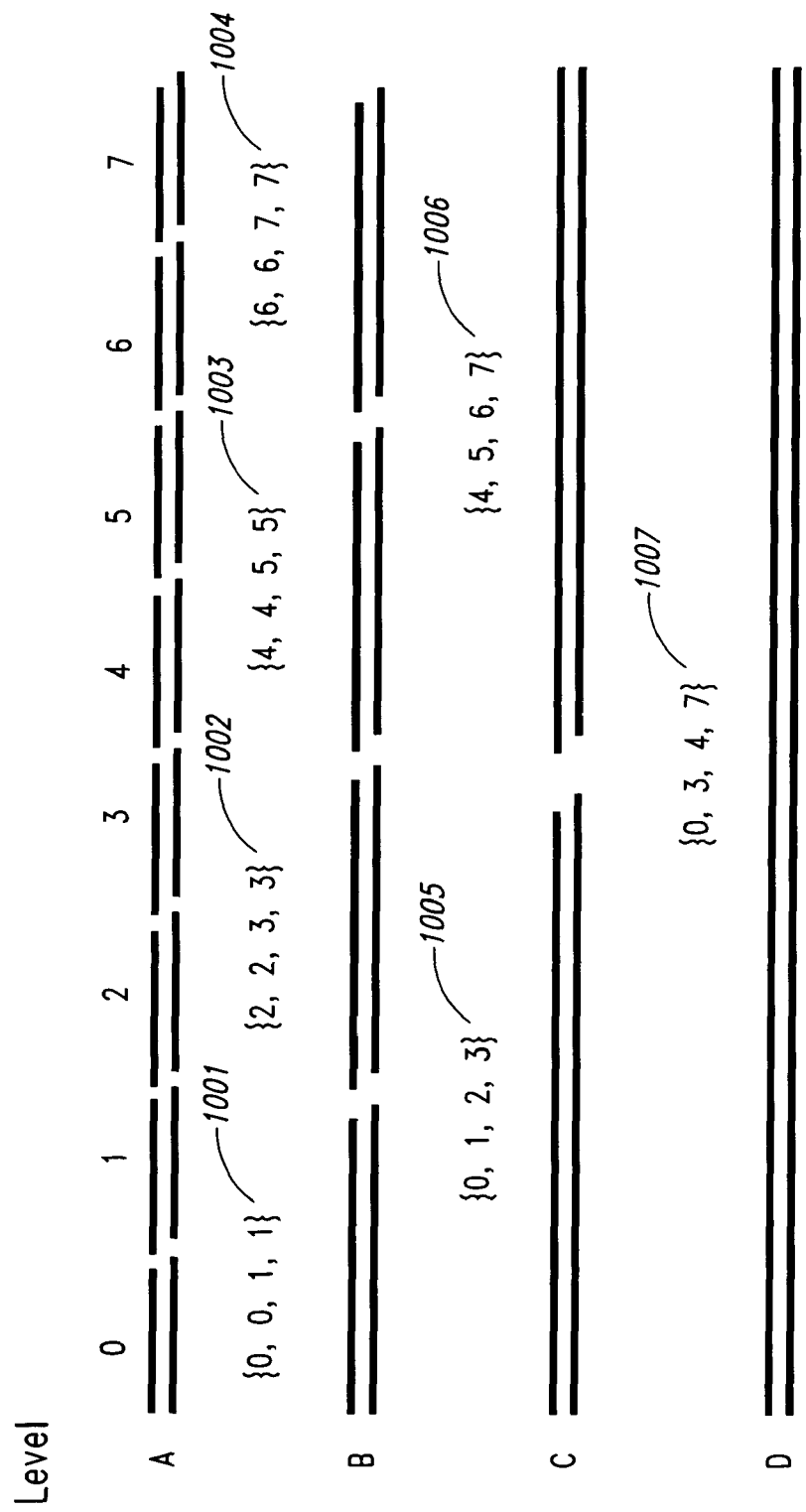
FIG. 10 is an example schematic for determining fragment set definitions for an example set of initial potential fragments.

FIG. 10 is an example schematic for determining fragment set definitions for an example set of initial potential fragments. The target sequence is denoted by the longest fragment, Level D. In step 903 of FIG. 9, the target is decomposed into the 8 initial potential fragments shown in Level A, labeled as fragments 0–7. To compute the fragment sets for the ligation reactions to be performed first (to create the next level, which here is shown as Level B), the groups of fragments to be ligated together to produce the next level are examined to determine which of the initial potential fragments 0–8 define the end sequences of these fragments. In the case of convergent synthesis, pairs of fragments are ligated. So, initial potential fragment pairs 0 and 1, 2 and 3, 4 and 5, and 6 and 7 (4 pairs) are to be ligated to produce Level B. To determine the fragment set definition for the first fragment pair ligation (fragments 0 and 1), the routine determines that the left end of fragment 0 is defined by fragment 0, the right end of fragment 0 is defined by fragment 0, the left end of fragment 1 is defined by fragment 1 and the right end of fragment 1 is defined by fragment 1. The other fragment set definitions for the remaining ligation reactions to produce Level B are similarly computed. At the next ligation level, the product ligations of Level B are paired and ligated to produce Level C. Thus the fragment set definition that defines the ends of interest for the first ligation reaction includes fragments 0, 1, 2, and 3, and is denoted as {0, 1, 2, 3}. Specifically, fragment 0 defines the left end of the first fragment of the ligation pair; fragment 1 defines the right end of the first fragment of the ligation pair; fragment 2 defines the left end of the second fragment of the ligation pair; and fragment 3 defines the right end of the second fragment of the ligation pair. The remaining fragment set definitions are determined in a similar manner. In summary, each fragment set definition provides a quick indicator to locate the end sequences for the ends that are being evaluated for participation in a ligation reaction and also provides an easy indicator of the fragments that surround an inner joint that may be potentially adjusted.

Returning to FIG. 9, once the fragment set definitions are determined, the routine in steps 905–907 loops over the fragment sets for each level, evaluates them against the synthesis criteria, and adjusts the potential fragments (or joints) until the potential fragments of each level satisfy the criteria or until no more adjustments can be performed. Specifically, in step 905, the routine determines whether there are more levels to process, and, if so, continues in step 906, else continues in step 908. In step 906, the routine calls a ProcessFragmentSets routine to perform the evaluation and adjustments for the fragment sets at that level and receives an indication of the success/failure of the evaluation. This routine is discussed further below with respect to FIG. 11. In one embodiment, this indication is a "score," whereby 0 indicates success and points are assigned against a fragment set for each different ligation failure mode. So, for example, each overhang ends combination that generates an incorrect ligation according to partial (3/4 base, 6/9 base, etc.) matching may generate a point, which are accumulated in a total score for that fragment set. In step 907, the next level to be processed is selected and the routine returns to the beginning of the loop in step 905. In step 908, the routine, after processing all of the fragment sets for all of the levels, determines a cumulative score for the entire potential design. In step 909, the routine determines whether the cumulative score indicates a successful potential design and, if so, returns, otherwise returns to the beginning of the loop in step 901 to try a new oligo length. In an alternative embodiment, in step 907, if the cumulative score for a particular level indicates failure, then the routine tries to readjust the joints in a previously examined level, and reevaluates the particular level that failed, before moving on to evaluate a new level. Other variations are also possible.

Figure 11:
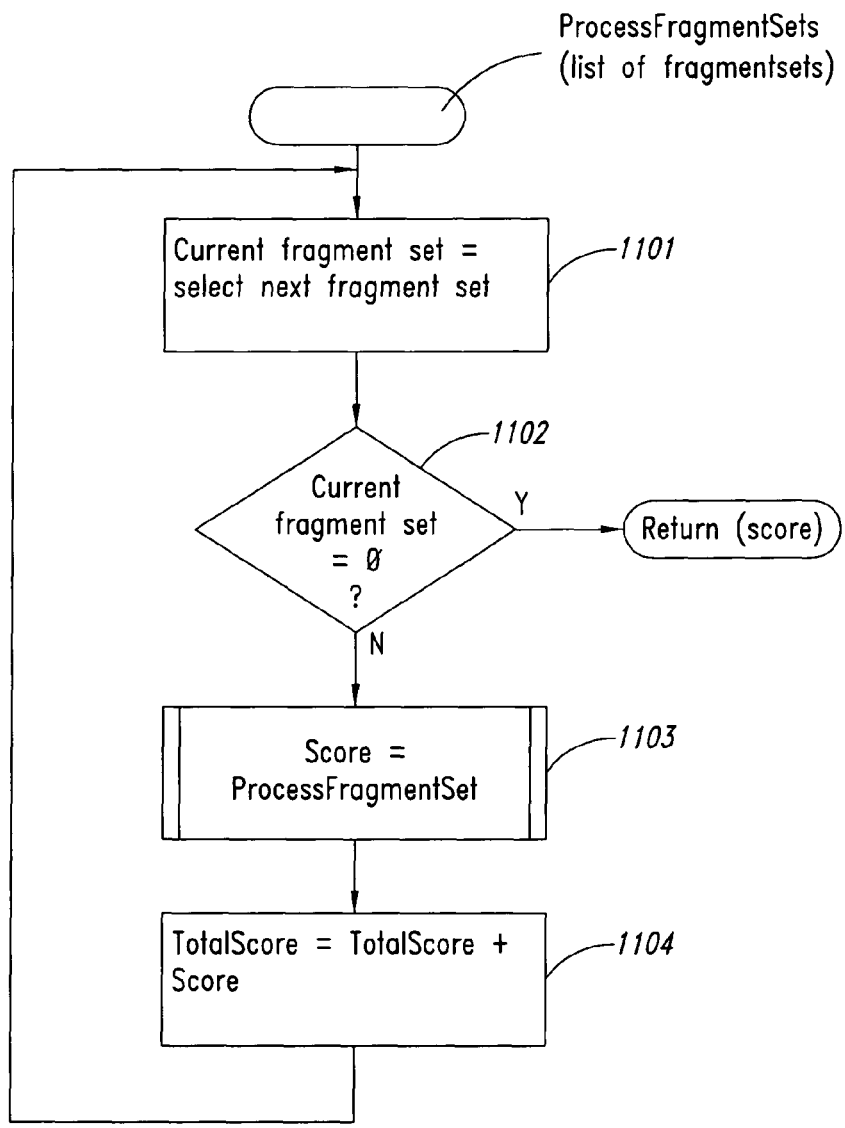
FIG. 11 is an example flow diagram of a routine for processing fragment sets.

FIG. 11 is an example flow diagram of a routine for processing fragment sets. For each fragment set in a designate list of fragments, the routine calls a routine to evaluate the fragment set, accumulates a "score" for the fragment sets in the list, and then returns the score. Specifically, in step 1101, the routine selects the next fragment set to process from the designated list. In step 1102, the routine determines whether there are any more to process (end of list), and, if so, returns the accumulated score, else continues in step 1103. In step 1103, the routine calls the ProcessFragmentSet routine to evaluate and individual fragment set and receives an evaluation score as described above. This routine is discussed further below with respect to FIG. 12. In step 1104, the accumulated score is incremented by the score received for the current fragment set and the routine returns to the beginning of the loop in step 1101.

Figure 12:
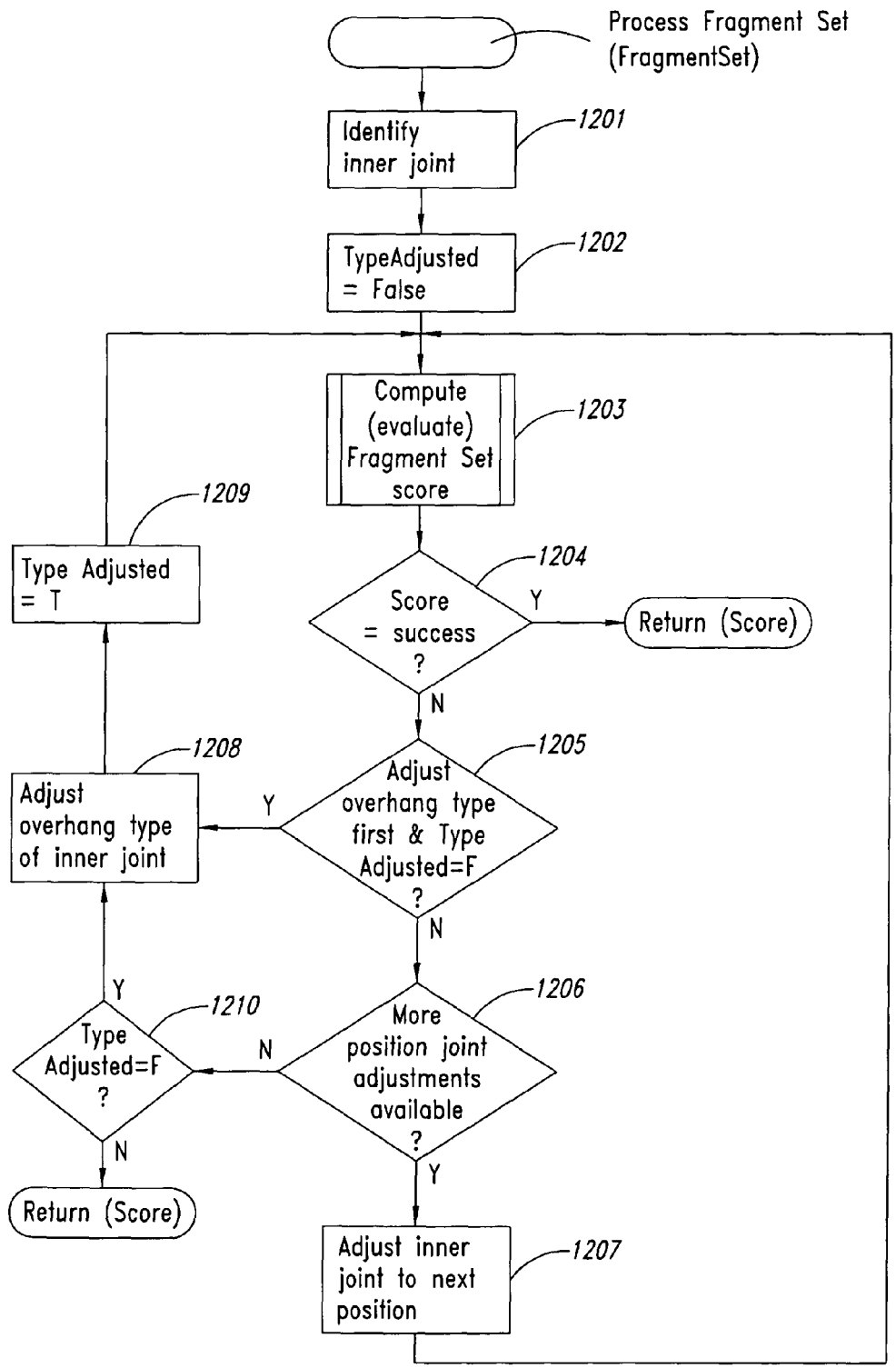
FIG. 12 is an example flow diagram of a routine for evaluating and adjusting the design of fragments referred to by a fragment set.

FIG. 12 is an example flow diagram of a routine for evaluating and adjusting the design of fragments referred to by a fragment set. In summary, the routine evaluates the predicted behavior of the ends that will be involved in the ligation reaction indicated by the inner joint of the fragment set and adjusts these potential fragments to optimize (or correct for) potentially unsuccessful ligation behavior. Different adjustment strategies may be used in conjunction with this routine. As shown, the routine allows for the adjustment of overhang type surrounding the joint to be performed prior to moving the position of the joint itself. One skilled in the art will recognize that other adjustments may be made that are not specifically discussed herein and are intended to fall within the scope of the invention and the techniques described. For example, the length of the ends of a fragment may be modified on a per-fragment basis.

Specifically, in step 1201, the routine identifies the "inner joint." This is the joint of the desired ligation reaction. Recall that each fragment set indicates the fragment that defines the left end of the first fragment of the ligation pair, the fragment that defines the right end of the first fragment of the ligation pair, the fragment that defines the left end of the second fragment of the ligation pair, and the fragment that defines the right end of the second fragment of the ligation pair. A fragment set is denoted thus herein as {$F1_L$, $F1_R$, $F2_L$, $F2_R$}. The ligation reaction being examined is the inner joint between ends $F1_R$ and $F2_L$. This joint specifies the ends that are needed to ligate successively for the potential design to be successful.

In step 1202, the routine initializes an indicator to indicate whether an overhang type adjustment has already been made. In steps 1203–1207, the routines loops to evaluate the fragment set according to the synthesis criteria and adjust the position of the joint. Steps 1209–1210 adjust the overhang type. Specifically, in step 1203, the routine calls a ComputerFragmentSetScore routine to evaluate the fragment set according to a set of synthesis criteria. This routine is discussed further below with respect to FIG. 15. In step 1204, the routine determines whether a successful evaluation (score) was returned, and, if so, the routine returns with the successful score, because no adjustments to the potential fragments involved in that ligation reaction are necessary. Otherwise, the routine continues in step 1205. In step 1205, the routine determines whether the runtime parameter to adjust overhang type first was set and whether this adjustment has not been made yet, and, if so, continues in step 1208, else continues in step 1206. In step 1206, the routine determines whether there are additional joint position adjustments that can be made, and if so, continues in step 1207, else continues in step 1210.

In step 1207, the joint position of the inner joint is adjusted. One technique for tracking potential joint position adjustments is to maintain a list of them associated with the fragment set definition and remove indicators to the adjustments that have already been made once they have been done. In one embodiment, joints are adjusted alternating between left and right adjustments. For example, the joints are adjusted by moving the joint position in the following order: left by 1, right by 1, left by 2, right by 2 . . . etc., until some limit or until the current oligo length indicates that there are no more joint positions.

Figure 13:
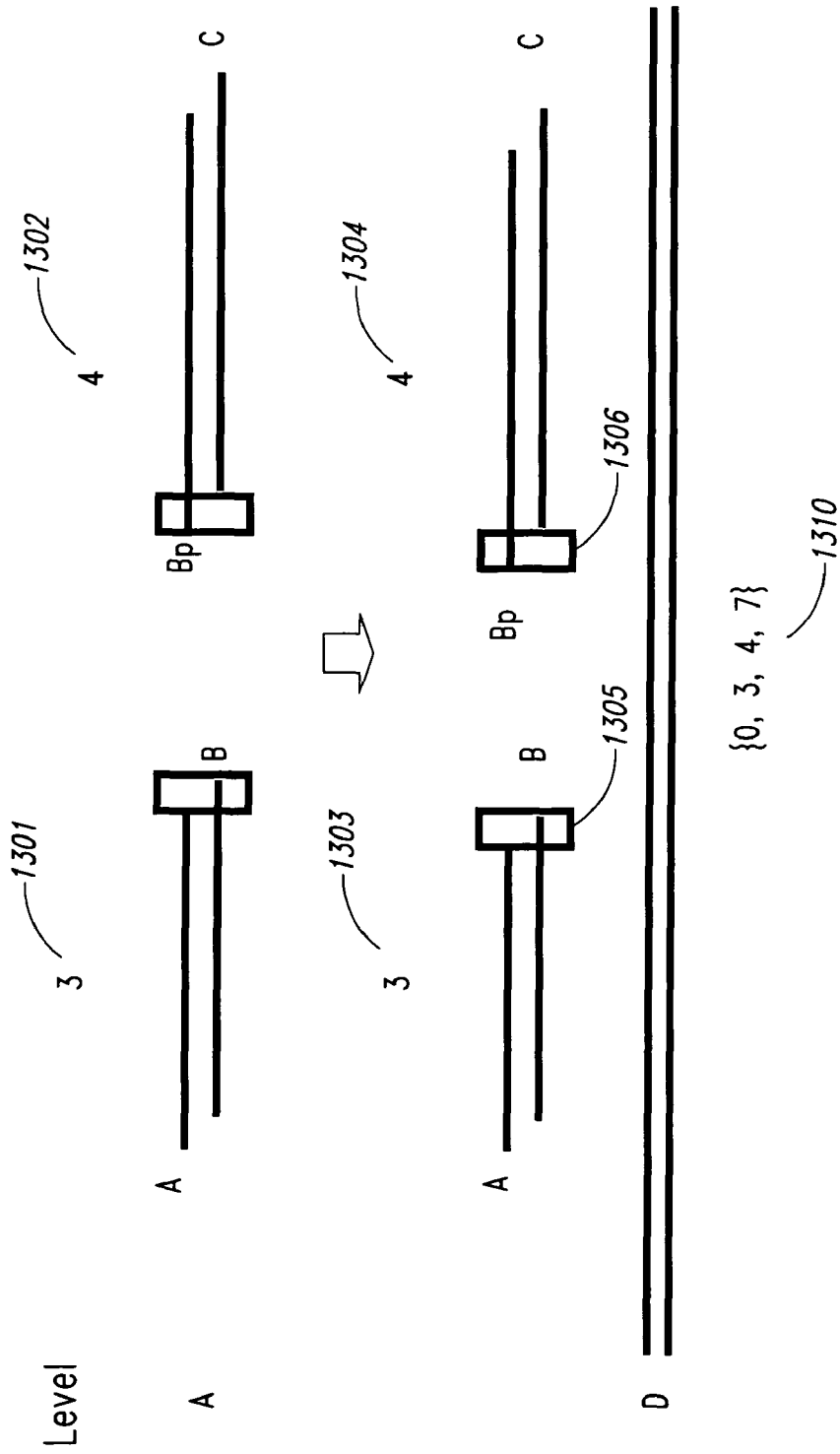
FIG. 13 is an example schematic of joint position adjustment.

FIG. 13 is an example schematic of joint position adjustment. In FIG. 13, the fragments participating in the designed ligation reaction are labeled fragment 3 and fragment 4. The fragment set definition 1310 (denoted {0, 3, 4, 7}) indicates that the inner joint is found between potential fragments 3 and 4 and that potential fragment 0 can be used to determine the left end sequence of the first fragment; potential fragment 3 can be used to determine the right end sequence of the first fragment; potential fragment 4 can be used to determine the left end sequence of the second fragment; potential fragment 7 can be used to determine the right end sequence of the second fragment. Fragments 1301 and 1302 represent the original potential fragments that have been evaluated to have undesired ligatability. Fragments 1303 and 1304 are these same fragments after the inner joint has been moved some number of positions to the left (for example, if the overhang left is 4 bases, then the picture depicts a move equal to the overhang length, or 4 bases). To perform the joint adjustment, the fragment definitions of fragments 3 and 4 are modified and updated to reflect the changed sequence and length of the fragment that is modified. For example, the modified fragment 1303 has 4 less bases on both the top and bottom strand, which bases are moved (copied) to the fragment definition sequences for the top and bottom strands of modified fragment 1304. In addition modified fragment 1303 reduced its length by 4; whereas modified fragment 1304 increased its length by 4. Thus, by changing fragment definitions, the joint is effectively moved. Alternate embodiments may store information on the joints as well as on the potential fragments and indicate changes accordingly.

In step 1208, the inner joint is instead adjusted in terms of the overhang type of the ends to participate in the ligation reaction. If, in step 1206 no more joint positions are possible, then the routine continues in step 1210 to determine whether the joint overhang type has already been adjusted. If so, the routine returns with an unsuccessful score, otherwise attempts the adjustment in step 1208.

Figure 14:
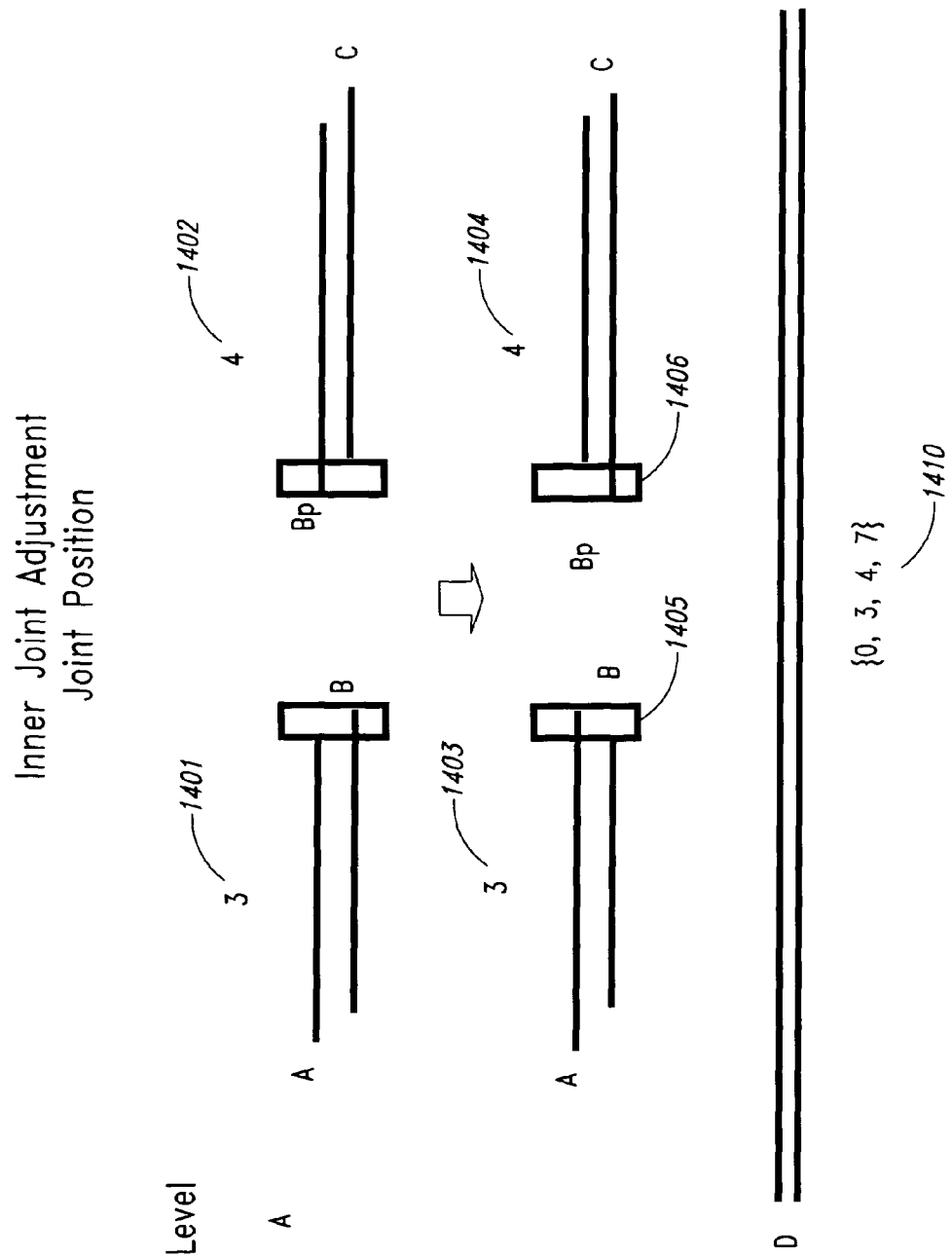
FIG. 14 is an example schematic of joint overhang type adjustment.

FIG. 14 is an example schematic of joint overhang type adjustment. The fragment set 1410 illustrated is the same as that discussed with respect to FIG. 13. Fragments 1401 and 1402 are modified to produce fragments 1403 and 1404 by reversing the "handedness" (the 3' or 5' directionality) of the ends involved in the inner joint. Hence, the overhang of fragment 1401 definition is modified from a 5' end of a sequence constituting the overhang (the direction of the bases of the bottom strand sequence that overhangs is from 5' to 3') to a 3' end constituting the overhanging portion. Correspondingly, the fragment definition of fragment 1402 is modified to have a 3' overhang on its left end. These modifications can be made by moving the indicators of bases off the strands of one fragment to another. Thus the indicators of bases eliminated from the top strand of fragment 1402 are copied to the top strand of fragment 1403; the indicators of bases eliminated from the bottom strand of fragment 1401 are copied to the bottom strand of fragment 1404.

Figure 15:
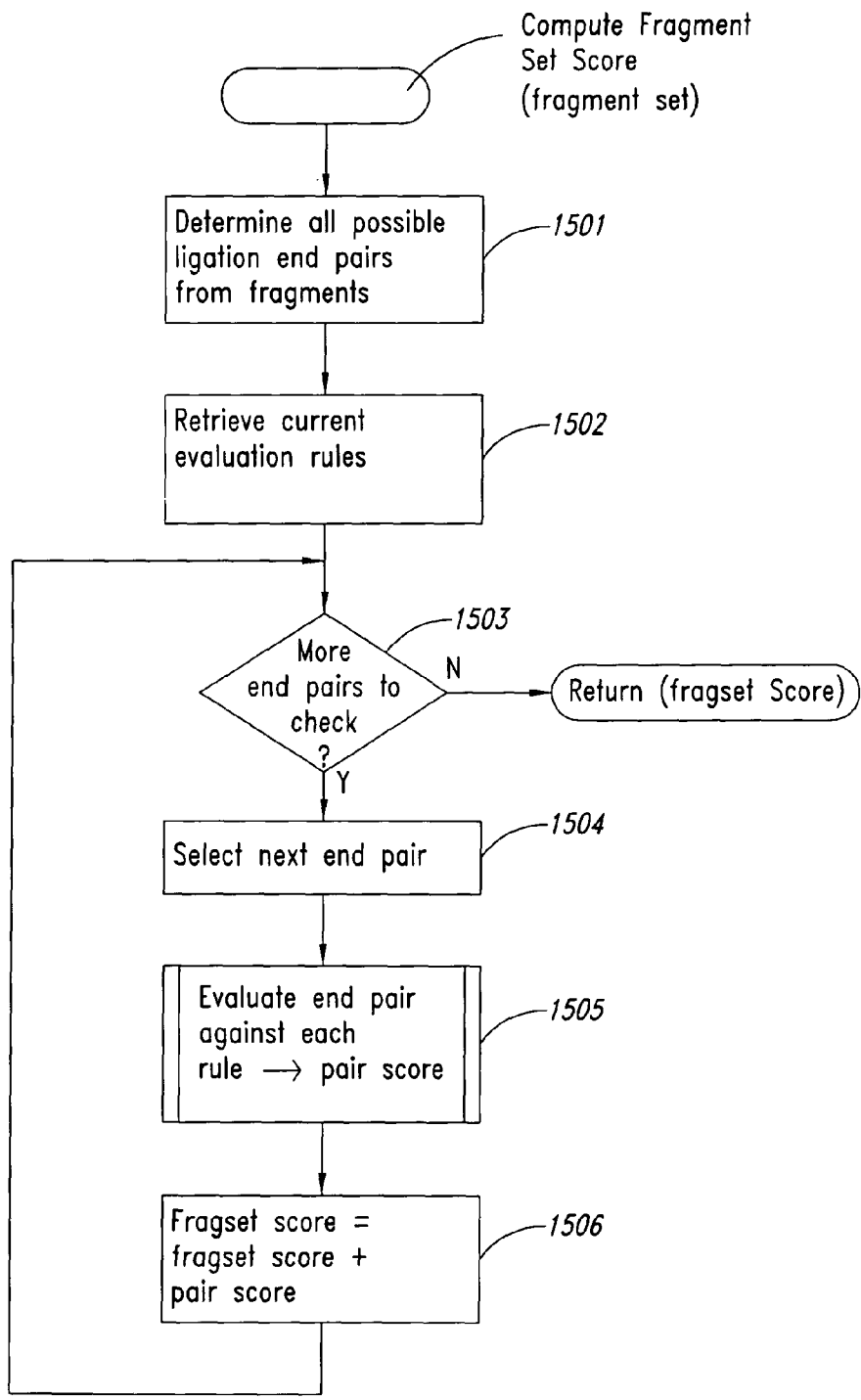
FIG. 15 is an example flow diagram for evaluating/scoring a fragment set.

FIG. 15 is an example flow diagram for evaluating/scoring a fragment set. As mentioned, the specifics of evaluating and indicating an outcome of the evaluation can be varied across implementations. The ComputerFragmentSetScore routine evaluates the designated fragment set against synthesis criteria and returns a score for the fragment set as a whole. In step 1501, the routine determines all of the possible ligation end pairs that can potential ligate. For a ligation involving a pair of fragments, such as with convergent synthesis techniques, the end pair combinations of interest are illustrated in FIG. 4. These end sequences may be conveniently stored as part of the fragment set definitions, or the can be determined from the potential fragments that are indicated by the fragment set definitions. In step 1502, the routine retrieves a current set of evaluation rules from, for example, a synthesis rule data repository. Having a separate rule specification allows rules to be modified and added dynamically to the system, especially as empirical evidence for new heuristics is found, or for example, to load the particular rules applicable to the synthesis technique being used in the design. For example, different rules (or additional rules) may be only applicable to one type of synthesis. In step 1503, the routine determines whether there are additional end pair combinations to examine and, if so, continues in step 1504, else returns the accumulated score for the fragment set. In step 1504, the routine selects the next end pair to examine. In step 1505, the routine calls another routine to evaluate the current end pair against each retrieved rule and to compute a score for that pair. In step 1505, the routine increments the score for the fragment set by the pair score and then returns to the beginning of the loop in step 1503 to process the next end pair.

Figure 16:
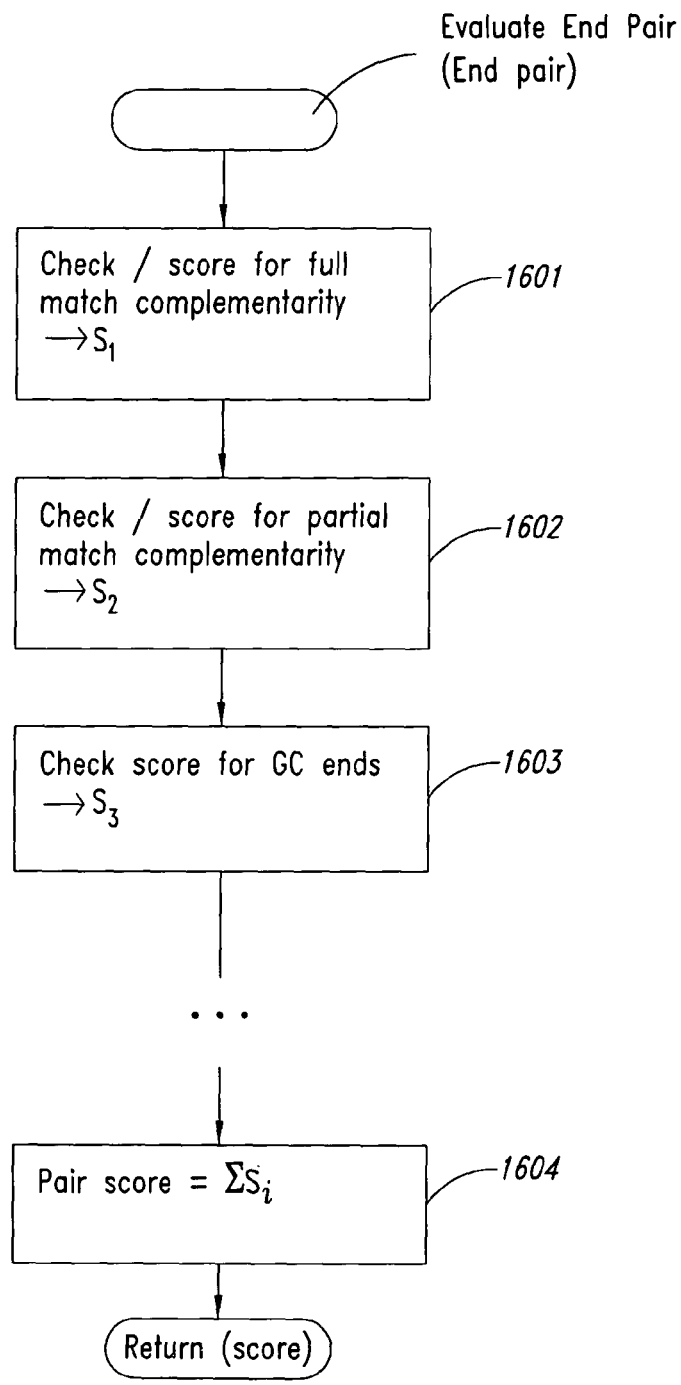
FIG. 16 is an example flow diagram of example synthesis rules used to evaluate ends of a pair of DNA fragments.

FIG. 16 is an example flow diagram of example synthesis rules used to evaluate ends of a pair of DNA fragments. One skilled in the art will recognize that any heuristics or rules could be incorporated into the APSDS engine in this manner. The current heuristics and rules shown in FIG. 16 are those that have been derived directly by trying ligation reactions for different n-mers in the laboratory or by extrapolating based upon observed failure modes for ligations that were designed but failed when brought into the laboratory. Thus, additional rules may be added, rules changed, or rules removed and yet still achieve the functions of the APSDS engine. Thus, in one embodiment, in step 1601, the routine checks a designated end pair for full match complementarity and saves the result. A "full" match means that all of the bases of the first end are complements of the bases of the second end. As described earlier, the complementarity evaluated by one embodiment includes both exact complementarity (traditional Watson-Crick base complements A/T and C/G) and approximate complementarity, which currently includes C/T and G/T bases as effective complements. One skilled in the art will recognize that as additional conditions are found in which cause ends to behave as though they are complements, then these conditions can be added to the tests for complementarity. In step 1602, the routine checks a designated end pair for partial match complementarity and saves the result. A "partial" match means that only a portion (determined by the rules) of the bases of the first end are complements of the bases of the second end. The rules are coded to indicate whether the portion needs be consecutive. For example, a 75% match (3/4 base pairs) could be a match of bases in positions 1,2 and 4 or a match of bases in consecutive position 1, 2, and 3. Currently, 3/4 and 6/9 partial matches are detected. In step 1603, the routine checks a designated end pair for the presence of GC ends and saves the result.

As indicated, other steps can be performed to include other end pair checking. In one embodiment, a lookup table is provided for combinations that have been physically tested in the laboratory and shown to cause either a successful or an unsuccessful ligation. In a current embodiment of the APSDS, a lookup table is provided for ends of overhang length 2 (i.e., 2-mers), where there are 256 possible 2-mer combinations for overhangs formed from A, G, C and T. In step 1604, the saved results of the evaluations are accumulated, and then returned.

EXAMPLES

Example 1

Synthesis of 5'-Phosphorylated Oligonucleotides and Formation of Duplex Fragments The oligonucleotides used in the ligation experiments are prepared using an Oligo 1000M DNA Synthesizer (Beckman Coulter, Inc, Fullerton, Calif.) using Beckman 30 nM DNA Synthesis Columns. All standard phosphoramidites and ancillary synthesis reagents are obtained from Glen Research, Inc. (Sterling, Va.). Chemical phosphorylation of the oligonucleotides is done with the Chemical Phosphorylation II (Glen Research). Concentrated ammonia is obtained from Fisher Scientific (Springfield, N.J.). 40% N-methylamine is obtained from Fluka Chemical Corporation (Milwaukee, Wis.). After cleavage from the solid support, the oligonucleotides are Trityl On purified using Poly-Pak Cartridges according to the instruction manual provided by Glen Research. Reagents for Trityl On purification are HPLC-grade acetonitrile and water obtained from Burdick & Jackson (Muskegon, Mich.). Triethylammonium acetate (TEAA), pH 7.0, and 3% Trifluoroacetic acid in water are obtained from Glen Research. After purification, the synthesized oligonucleotides are evaporated to dryness in a SpeedVac (Savant, Farmingdale, N.Y.) and resuspended in HPLC grade water. Concentrations of the oligonucleotides are determined by reading the 260 nm absorbance on a Pharmacia LKB Ultrospec III (Amersham Pharmacia, Upsala, Sweden).

The oligonucleotides are used to form duplex fragments by drying 500 pmoles each of the complementary oligonucleotides in a speedvac and resuspending in 10 microliters TE. A 5 microliter sample of the solution (250 pmoles) is mixed with 10 microliters of 2×SSPE (prepared according to Manniatis), heated to 95° C. and cooled to room temperature.

Example 2

Ligation Experiments

For every two fragments (designated A and B) there are 3 ligation experiments: 2 self ligations (A alone and B alone) and a normal ligation (A combined with B). Each ligation uses 500 picomoles of a pair of double-stranded oligonucleotides, i.e., a DNA fragment, 3 microliters of 10× ligation buffer (Fermentas Inc., Hanover, Md.), 10 units of T4 DNA ligase (product # EL0016, Fermentas) and water to make a total volume of 30 microliters. All duplexes are ligated together under the same conditions. Each ligation mix is incubated at 37° C. for 60 minutes, heated to 65° C. for 10 minutes.

The results from this set of ligation experiments are evaluated to determine the overhangs present in A and B will tend to undergo normal ligation or self ligation. The procedure can be followed for any set of possible overhang sequences. When the overhang has only two nucleotides, then there are 16 possible overhang sequences in each fragment end, and with two fragments there are 256 normal ligation experiments to perform. When the overhang has three nucleotides, there are 64 different possible overhang sequences in each fragment, with 4,096 different normal ligation experiments to perform. When the overhang has four nucleotides, there are 65,536 normal ligation experiments to perform. As the number of experiments increases, recourse may be made to robotics to speed up the time needed to run an experiment and/or relieve the tedium of running the experiments.

All of the above U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 60/278,086 filed Mar. 22, 2001 and U.S. Provisional Patent Application No. 60/278,067 filed Mar. 22, 2001, are incorporated herein by reference, in their entirety.

From the foregoing it will be appreciated that, although specific embodiments of the invention have been described herein for purposes of illustration, various modifications may be made without deviating from the spirit and scope of the invention. For example, one skilled in the art will recognize that the methods and systems discussed herein are applicable to other types of gene synthesis, including solid phase and shotgun synthesis. One skilled in the art will also recognize that the methods and systems discussed herein are applicable to differing protocols, communication media (optical, wireless, cable, etc.) and to devices for interfacing to synthesis process and for managing the data entry and synthesis design output (such as wireless handsets, electronic organizers, personal digital assistants, portable email machines, game machines, pagers, navigation devices such as GPS receivers, etc.). Accordingly, the invention is not limited except as by the appended claims.

The invention claimed is:

1. A method in a computer system for automated generation of a design for synthesizing a designated target double-stranded polynucleotide molecule according to a convergent synthesis technique, comprising:

decomposing the designated target molecule into a plurality of potential double-stranded fragments, each fragment having an associated fragment definition and having ends that will potentially ligate with ends of other fragments;

automatically determining whether the potential double-stranded fragments satisfy a plurality of synthesis criteria for synthesizing fragments and generating an indication of the determination;

when the indication indicates that the potential fragments do not satisfy the synthesis criteria, automatically adjusting the fragment definitions of the plurality of potential fragments thereby adjusting at least one joint of the designated target molecule and repeating the automatically determining whether the potential fragments satisfy the plurality of synthesis criteria, the generating the indication of determination, and the automatically adjusting the fragment definitions until the generated indication indicates that the plurality of potential fragments will synthesize properly to create the designated polynucleotide molecule; and generating a design output that indicates the polynucleotide sequences of the plurality of potential fragments as defined by the adjusted fragment definitions and an ordering for combining the plurality of polynucleotide sequences according to a convergent synthesis technique.

2. The method of claim 1 further comprising using the generated design output to automatically control a polynucleotide synthesizer apparatus.

3. The method of claim 1 wherein a fragment definition comprises, for each strand of the associated sequence fragment, an indication of a position in the designated target molecule, an indication of a nucleotide sequence, and an indication of length.

4. The method of claim 1 wherein the automatically adjusting the fragment definitions comprises adjusting at least one of overhang type, overhang length, joint position between a plurality of fragments, or a sequence of nucleotides in at least one strand of the fragment.

5. The method of claim 4 wherein overhang type is adjusted prior to the sequence.

6. The method of claim 4 wherein overhang type is adjusted prior to joint position.

7. The method of claim 4 wherein the sequence is adjusted prior to overhang type.

8. The method of claim 4 wherein the sequence is adjusted prior to joint position.

9. The method of claim 1 wherein the automatically determining whether the potential fragments satisfy the plurality of synthesis criteria incorporates ends-checking rules to determine the ligatability of a plurality of groups of potential fragments.

10. The method of claim 1 wherein the synthesis criteria specify empirically-based ligation rules.

11. The method of claim 1 wherein the synthesis criteria comprises rules that check for approximate complementarity between base pairs of fragment overhangs of a group of potential fragments.

12. The method of claim 11 wherein the rules determine full matches between the base pairs of the fragment overhangs.

13. The method of claim 11 wherein the rules determine partial matches between the base pairs of the fragment overhangs.

14. The method of claim 13 wherein a partial match between two fragment overhangs occurs when three of four base pairs of the respective fragment overhangs are complementary and at least one of three bases of the fragment overhang of the first fragment is approximately complementary to one of three bases of the fragment overhang of the second fragment.

15. The method of claim 13 wherein a partial match between two fragment overhangs occurs when three of four base pairs of the respective fragment overhangs are complementary.

16. The method of claim 13 wherein a partial match between two fragment overhangs occurs when six of nine base pairs of the respective fragment overhangs are complementary.

17. The method of claim 11 wherein approximate complementarity between base pairs of two fragment overhangs is detected when at least one of an C-T base pair and an G-T base pair is present.

18. The method of claim 11 wherein approximate complementarity between base pairs of two fragment overhangs is detected when a first base is empirically found under synthesis conditions to behave as a recognized mate of a second base but is not a recognized mate, where A and T are recognized mates and G and C are recognized mates, and the first base is present in the first fragment overhang and the second base is present in the second fragment overhang.

19. The method of claim 1 wherein the synthesis criteria are dynamically determined.

20. The method of claim 1 wherein the synthesis criteria comprise ends-checking rules that are derived empirically.

21. The method of claim 1 wherein the synthesis criteria comprise a rule for determining the presence of G or C base in mating positions when the overhangs of two fragments are annealed together.

22. The method of claim 1 wherein the indication of the determination of whether the potential fragments satisfy the synthesis criteria generates a score.

23. The method of claim 22 wherein a separate score is generated each time the fragment definitions are adjusted.

24. A computer-readable memory medium containing instructions for controlling a computer processor, when executed, to automatically generate a design for synthesizing a designated target double-stranded polynucleotide molecule according to a convergent synthesis technique, by performing a method comprising:

decomposing the designated target molecule into a plurality of potential double-stranded fragments, each fragment having an associated fragment definition and having ends that will potentially ligate with ends of other fragments;

automatically determining whether the potential double-stranded fragments satisfy a plurality of synthesis criteria for synthesizing fragments and generating an indication of the determination;

when the indication indicates that the potential fragments do not satisfy the synthesis criteria, automatically adjusting the fragment definitions of the plurality of potential fragments thereby adjusting at least one joint of the designated target molecule and repeating the automatically determining whether the potential fragments satisfy the plurality of synthesis criteria, generating the indication of the determination and the automatically adjusting the fragment definitions until the generated indication indicates that the plurality of potential fragments will synthesize properly to create the designated polynucleotide molecule; and generating a design output that indicates the polynucleotide sequences of the plurality of potential fragments as defined by the adjusted fragment definitions and an ordering for combining the plurality of polynucleotide sequences according to a convergent synthesis technique.

25. The memory medium of claim 24 further comprising using the generated design output to automatically control a polynucleotide synthesizer apparatus.

26. The memory medium of claim 24 wherein a fragment definition comprises, for each strand of the associated sequence fragment, an indication of a position in the designated target molecule, an indication of a nucleotide sequence, and an indication of length.

27. The memory medium of claim 24 wherein the automatically adjusting the fragment definitions comprises adjusting at least one of overhang type, overhang length, joint position between a plurality of fragments, or a sequence of nucleotides in at least one strand of the fragment.

28. The memory medium of claim 24 wherein the automatically determining whether the potential fragments satisfy the plurality of synthesis criteria incorporates rules to determine the ligatability of a plurality of groups of potential fragments.

29. The memory medium of claim 28 wherein the rules comprise at least one of empirically-based ligation rules, rules that check for approximately complementarity between base pairs of fragment overhangs of a group of potential fragments, rules that are dynamically determined, or ends-checking rules that are derived empirically.

30. The memory medium of claim 29 wherein the rules that check for approximate complementarity determine full matches between the base pairs of fragment overhangs.

31. The memory medium of claim 29 wherein the rules that check for approximate complementarity determine partial matches between the base pairs of fragment overhangs.

32. The memory medium of claim 24 wherein the indication of the determination of whether the potential fragments satisfy the synthesis criteria generates a score.

33. A computer system for generating a design for synthesizing a designated target double-stranded polynucleotide molecule according to a convergent synthesis technique, comprising:
  a synthesis rule data repository that contains a plurality of synthesis criteria for synthesizing fragments according to the convergent synthesis technique;
  a synthesis design engine that is configured to,
    decompose the designated target molecule into a plurality of potential double-stranded fragments, each fragment having an associated fragment definition and having ends that will potentially ligate with ends of other fragments;
    retrieve at least one of the plurality of synthesis criteria from the synthesis rule data repository;
    automatically determine whether the potential double-stranded fragments satisfy the at least one synthesis criteria and generate an indication of the determination;
    when the indication indicates that the potential fragments do not satisfy the synthesis criteria, automatically adjust the fragment definitions of the plurality of potential fragments thereby adjusting at least one joint of the designated target molecule and repeat the automatic determination of whether the potential fragments satisfy the synthesis criteria, the generation of the indication of the determination, and the automatic adjustment of the fragment definitions until the generated indication indicates that the plurality of potential fragments will synthesize properly to create the designated polynucleotide molecule; and
    generate a design output that indicates the polynucleotide sequences of the plurality of potential fragments as defined by the adjusted fragment definitions and an ordering for combining the plurality of polynucleotide sequences according to a convergent synthesis technique; and
  a synthesis design data repository that receives and stores the generated design output.

34. The computer system of claim 33 further comprising a control system that receives the generated design output from synthesis design data repository and uses generated design output to automatically control a polynucleotide synthesizer apparatus.

35. The computer system of claim 33 wherein a fragment definition comprises, for each strand of the associated sequence fragment, an indication of a position in the designated target molecule, an indication of a nucleotide sequence, and an indication of length.

36. The computer system of claim 33 wherein the automatic adjustment of the fragment definitions comprises adjusting at least one of overhang type, overhang length, joint position between a plurality of fragments, or a sequence of nucleotides in at least one strand of the fragment.

37. The computer system of claim 33 wherein the plurality of synthesis criteria for synthesizing fragments contained in the synthesis rule data repository incorporates rules that can be used to determine the ligatability of a plurality of groups of potential fragments.

38. The computer system of claim 37 wherein the rules comprise at least one of empirically-based ligation rules, rules that check for approximately complementarity between base pairs of fragment overhangs of a group of potential fragments, rules that are dynamically determined, or ends-checking rules that are derived empirically.

39. The computer system of claim 38 wherein the rules that check for approximate complementarity determine full matches between the base pairs of fragment overhangs.

40. The computer system of claim 38 wherein the rules that check for approximate complementarity determine partial matches between the base pairs of fragment overhangs.

41. The computer system of claim 33 wherein the generated indication of the determination of whether the potential fragments satisfy the synthesis criteria generates a score.

* * * * *

UNITED STATES PATENT AND TRADEMARK OFFICE
CERTIFICATE OF CORRECTION

PATENT NO. : 7,164,992 B1 Page 1 of 1
APPLICATION NO. : 10/104986
DATED : January 16, 2007
INVENTOR(S) : Mulligan et al.

It is certified that error appears in the above-identified patent and that said Letters Patent is hereby corrected as shown below:

Column 28
Line 33, "synthesis criteria, generating" should read as -- synthesis criteria, the generating --.

Signed and Sealed this

Nineteenth Day of August, 2008

JON W. DUDAS
*Director of the United States Patent and Trademark Office*